(12) United States Patent
Yoshioka et al.

(10) Patent No.: US 6,228,968 B1
(45) Date of Patent: May 8, 2001

(54) SILANE COPOLYMER AND A METHOD FOR PRODUCING THE SAME

(75) Inventors: Masato Yoshioka; Hiroshi Shintani; Akihiro Segawa; Terumi Yoshihara, all of Osaka (JP)

(73) Assignee: Seiwa Kasei Company, Ltd., Osaka (JP)

( * ) Notice: Subject to any disclaimer, the term of this patent is extended or adjusted under 35 U.S.C. 154(b) by 0 days.

(21) Appl. No.: 09/245,418

(22) Filed: Feb. 5, 1999

(30) Foreign Application Priority Data

| Feb. 6, 1998 | (JP) | 10-041064 |
| Feb. 17, 1998 | (JP) | 10-052735 |
| Jun. 19, 1998 | (JP) | 10-172498 |

(51) Int. Cl.[7] .................................................. C08G 77/26
(52) U.S. Cl. ........................ 528/38; 424/401; 424/70.12; 514/2
(58) Field of Search ................. 528/38; 514/2; 424/401, 70.12

(56) References Cited

U.S. PATENT DOCUMENTS

| 5,220,033 | * | 6/1993 | Kamei et al. | 548/406 |
| 5,243,028 | * | 9/1993 | O'Lenick, Jr. | 530/375 |
| 5,580,921 | * | 12/1996 | Stepp et al. | 524/731 |
| 5,753,214 | | 5/1998 | Yoshioka et al. | 424/70.2 |

FOREIGN PATENT DOCUMENTS

| 0699431 | 3/1996 | (EP) . |
| 3223207 | 10/1991 | (JP) . |
| 03223207 | 12/1991 | (JP) . |
| 07223921 | 8/1995 | (JP) . |

* cited by examiner

Primary Examiner—Margaret G. Moore
(74) Attorney, Agent, or Firm—Birch, Stewart, Kolasch & Birch, LLP

(57) ABSTRACT

A silane copolymer is described which is usable, for example, as an ingredient of cosmetics for skin, hair or the like; obtainable by polycondensing one or more organic silane compounds having a hydrophilic group represented by the following general formula (I):

$$R^1_{(3-m)}Si(OH)_m A\text{—}B \qquad (I)$$

wherein m represents 2 or 3, $R^1$ represents an alkoxy group, a hydrogen atom or an alkyl group, A is a connecting moiety and represents a methylene group or the like, and B represents a hydrophilic organic group with one or more silane compounds represented by the following general formula (III):

$$R^2_n Si(OH)_p Y_{(4-p-n)} \qquad (III)$$

wherein n represents an integer from 0 to 2, p represents an integer from 2 to 4, $n+p \leq 4$, $R^2$ represents an organic group in which a carbon atom is directly connected to the silicon atom, and Y represent at least one group selected from the group consisting of an alkoxy group, hydrogen atom and siloxy group and when 4-p-n is 2; and optionally further reacting the resulting copolymer with one or more silane compounds represented by the following general formula (V):

$$R^3_3 Si(OH) \qquad (V)$$

wherein, $R^3$ represent an organic group in which a carbon atom is directly connected to the silicon atom. A method for producing the same is also described.

15 Claims, 11 Drawing Sheets solid line : silane copolymer
broken line : raw material solid line : silane copolymer
broken line : raw material solid line : silane copolymer
broken line : raw material solid line : silane copolymer
broken line : raw material solid line : silane copolymer
broken line : raw material

SILANE COPOLYMER AND A METHOD FOR PRODUCING THE SAME

TECHNICAL FIELD

The present invention relates to a silane copolymer and a method for producing the same. More particularly, the present invention relates to a silane copolymer which is obtainable by polycondensing, in an aqueous solution, one or more organic silane compounds (I) having a hydrophilic organic group and at least two hydroxyl groups directly bonded to a silicon atom with one or more silane compounds (III) having at least two hydroxyl groups directly bonded to a silicon atom; and a silane copolymer which is obtainable by polycondensing, in an aqueous solution, one or more organic silane compounds (I) with one or more silane compounds (III), then by allowing this resulting organic silane compound-silane copolymer to further cause addition reaction with one or more silane compounds (V) having one hydroxyl group directly bonded to a silicon atom, wherein the composition is endowed with properties based on the silane compound(III) in addition to properties based on the organic silane compound(V) having the hydrophilic group; and a method for producing the same.

PRIOR ART

Conventionally, a polypeptide is used in cosmetics for providing adsorption properties to hair, reducing, skin irritation providing protection by by film forming, providing moisture retention and the like based on the properties of the polypeptide. In addition to the polypeptide, silicone oils (organic silicone compound), various polymers, surfactants and the like are compounded into cosmetics to give cosmetics the properties of these compounding agents in addition to the properties of the polypeptide. However, there has been a problem in that some compounding agents are incompatible with the polypeptide and the properties of the compounding agents and the polypeptide can not be fully manifested.

For example, though a silicone oil has excellent extending property, luster and gloss providing properties, protecting properties by providing water repellency, and the like, since the silicone oil is originally a hydrophobic (lipophilic) substance and incompatible with a hydrophilic polypeptide, aqueous cosmetics compounding the silicone oil lack emulsion stability, even if an emulsifier is compounded together and value as commercial cosmetics is easily lost. Further, a polypeptide in cosmetics is not easily adhered to parts which have been contacted with the silicone oil in cosmetics previously, and inversely, the silicone oil is not easily adhered to parts which have been contacted with the polypeptide previously. Therefore, properties of both components can not be fully manifested.

For solving the above-mentioned problems, a polyoxyalkylene-modified silicone into which a polyoxyalkylene is introduced for the purpose of imparting hydrophilicity to a silicone is used in water-soluble cosmetics. However, this silicone is not easily adsorbed onto hair and skin since it does not have ionicity unlike a polypeptide.

For solving these problems, it is also suggested that a hydrophobic silicone oil is reacted with a hydrophilic polypeptide to synthesize a peptide-modified silicone derivative having properties of the silicone oil and properties of the polypeptide together, in order to solve defects occurring when a silicone oil and a polypeptide are compounded together and to manifest properties of the silicone oil and properties of the polypeptide (JP-A-3-223207).

However, the above-described peptide-modified silicone derivative disclosed in JP-A-3-223207 has a problem in that it causes turbidity and precipitation in storage since pH stability and storage stability thereof in water are poor due to the influence of the silicone portion, which is poorly soluble or insoluble in water, and since hair cosmetics and skin cosmetics are usually water-soluble. Further, there is also a problem in that production of the above-described peptide-modified silicone derivative shows poor reactivity and consequently gives low yield since this production is carried out in water by reacting a silicone oil, which is poorly soluble or insoluble in water, with a water-soluble polypeptide. Therefore, for improving the yield, a water-soluble organic solvent such as alcohol and the like should be added.

For solving these problems, the present inventors have produced, in an aqueous solvent, a silylated peptide in which a functional group containing only one silicon atom is connected to an amino group in a peptide by a covalent bond (JP-A-8-59424 and 8-67608), and which is usable as a base material of cosmetics and in a fiber treating agent.

However, this silylated peptide is inferior to a silicone oil in extending property and smoothness imparting property since it contains a small amount of silyl groups bonded to a peptide chain though it manifests excellent adsorbability onto hair and skin.

On the other hand, it has also been suggested that a polypeptide derivative endowed with properties other than property of a polypeptide is prepared by adding a fatty acid and a functional group to a polypeptide or by effecting esterification, and the polypeptide derivative is compounded in cosmetics to utilize adsorption action onto hair and skin owned by the polypeptide and to manifest the above-described properties on hair and skin. For example, a quaternary ammonium derivative of a peptide, fatty acid acylated derivative of a peptide, esters of a peptide and the like have been widely used in cosmetics.

However, since sites on the polypeptide to which functional groups are introduced are limited, functional groups can not be added, over a certain amount and the properties to be added to a polypeptide have been limited.

Further, adding two or more properties in addition to properties originally owned by a polypeptide and manifesting all properties have been desired.

Problem to be Solved by the Invention

Accordingly, an object of the present invention is to provide a compound which has an desirable property in addition to excellent properties of a silicone compound and a polypeptide, and which can be easily produced in an aqueous system without using an organic solvent and the like.

Means to Solve the Problem

The present inventors have been intensively studied to solve the above-described problem, and, as a result, have found that a silane copolymer defined below can attain this object. The present invention was thus completed.

The present invention provides:

a silane copolymer (T) which is obtainable by polycondensing
one or more organic silane compounds(I) having a hydrophilic group represented by the following general formula (I):

$$R^1_{(3-m)}Si(OH)_m A\text{—}B \qquad (I)$$

wherein m represents 2 or 3, $R^1$ represents an alkoxy group, a hydrogen atom or an alkyl group having 1 to 3 carbon atoms, A is a connecting moiety and represents at least one group selected from the group consisting of a methylene group, propylene group, —(CH$_2$)$_3$OCH$_2$CH(OH)CH$_2$—, —(CH$_2$)$_3$S—, —(CH$_2$)$_3$NH— and —(CH$_2$)$_3$OCOCH$_2$CH$_2$—, and B represents a hydrophilic organic group
with
one or more silane compounds(III) represented by the following general formula (III):

$$R^2{}_nSi(OH)_pY_{(4-p-n)} \quad (III)$$

wherein n represents an integer from 0 to 2, p represents an integer from 2 to 4, n+p≦4, R$^2$ represents an organic group in which a carbon atom is directly connected to the silicon atom and when n is 2, the two R$^2$ groups may be the same or different, and Y represent at least one group selected from the group consisting of an alkoxy group, hydrogen atom and siloxy group and when 4-p-n is 2, the Y groups may be the same or different.

By the above silane copolymer, excellent properties based on the organic silane compound represented by the general formula (I) and properties based on the silane compound represented by the general formula (III) are together obtained, and further, an additional property can also be manifested by the added functional group of the silane compound (III).

The present inventors have also found that a silane copolymer excellent in storage stability can be obtained by adding a silane compound having one hydroxyl group to the hydroxyl group in the silane copolymer(T).

Thus, present invention also provides:
a silane copolymer (U) which is obtainable by polycondensing
one or more organic silane compounds(I) having a hydrophilic group represented by the general formula (I) with one or more silane compounds(III) represented by the general formula (III); and then,
one or more silane compounds represented by the following general formula (V):

$$R^3{}_3Si(OH) \quad (V)$$

wherein, R$^3$ represent an organic group in which a carbon atom is directly connected to the silicon atom and the three R$^3$ groups may be same or different, is reacted with the resulting silane copolymer.

As mentioned above, by adding a silane compound represented by the general formula (V) to the hydroxyl group in the silane copolymer(T), a silane copolymer excellent in storage stability can be obtained.

PREFERABLE EMBODIMENTS OF THE INVENTION

Figure 1:
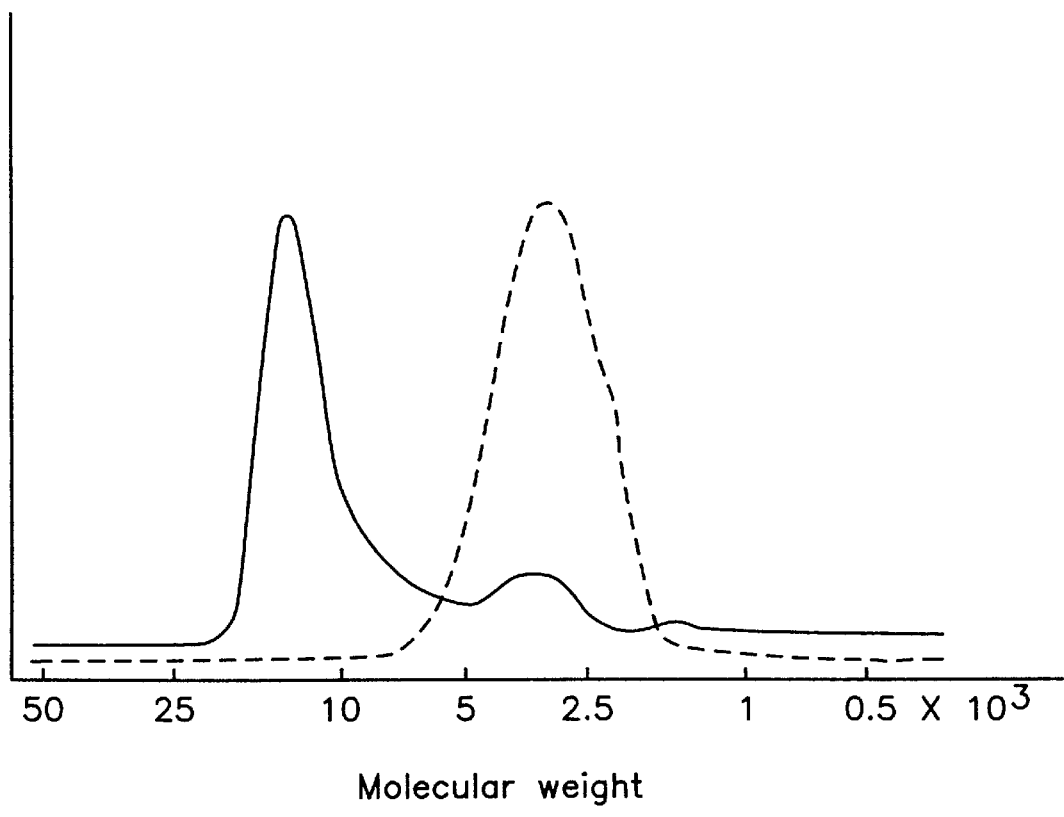
FIG. 1 is the results of gel filtration analysis of the silane copolymer obtained in Example 1 and the raw material used in Example 1.

The organic silane compound having a hydrophilic group represented by the general formula (I) is generally called a silyl compound. Some kinds of the organic silane compound (I) may be obtained by hydrolysis of a silane compound represented by the following general formula (VI):

$$R^4{}_3SiA\text{—}B \quad (VI)$$

wherein R$^4$ represents a hydroxyl group, alkoxy group, halogen group, hydrogen atom or alkyl group having 1 to 3 carbon atoms, the three R$^4$ groups may be the same or different, provided that at least two of three R$^4$ represent an alkoxy group or halogen group, and A and B are as defined in the formula (I). Other kinds of the organic silane compound (I) may be obtained not from the silane compound represented by the general formula (VI).

Examples of the hydrophilic organic group represented by B connected by the connecting moiety A in the above-described general formula (I) include protein, peptide or derivatives thereof, polyamino acid, saccharides, polyoxyalkylene ether, carboxylic acid or salts and derivatives thereof, sulfuric acid or salts and derivatives thereof, phosphoric acid or salts and derivatives thereof, sulfonic acid or salts and derivatives thereof, amine or salts thereof, polyamine or salts thereof, and the like.

Among the organic silane compounds having a hydrophilic group represented by the above-described general formula (I), those having a peptide as the organic group having a hydrophilicity represented by B manifest extremely excellent properties, when the resulting silane copolymer is used as a raw material of cosmetics, since the peptide has film forming action and excellent adsorbability onto skin and hair. Among the peptide, those having a number average molecular weight of 100–50,000 are particularly preferable.

Typical example of such silane compound represented by the general formula (I) in which the organic group having hydrohpilicity is a peptide or derivative thereof include silylated peptides represented by the following general formula (VII):

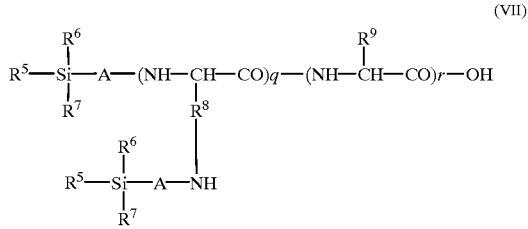

(VII)

wherein at least two of $R^5$, $R^6$ and $R^7$ represent a hydroxyl group, and the remaining group represents an alkyl group having 1 to 3 carbon atoms, Re represents a residual group of a basic amino acid obtained by removing a terminal amino group of the basic amino acid having two or more amino group on the terminal of the amino acid, $R^9$ represents a residual group of an amino acid other than $R^8$, A is a connecting moiety and represents at least one group selected from the group consisting of —$CH_2$—, —$(CH_2)_3$—, —$(CH_2)_3OCH_2CH(OH)CH_2$—, —$(CH_2)_3S$—, —$(CH_2)_3NH$— and —$(CH_2)_3OCOCH_2CH_2$—, q is 0 to 500, r is 0 to 500 and q+r is 1 to 500, wherein q and r represent only the number of an amino acid and does not represent the order of amino acid sequence. These silylated peptides can be easily synthesized in an aqueous solution by methods disclosed in JP-A-8-59424 and 8-67608.

In the silylated peptide represented by the above-described general formula (VII), RB represents a-residual group of a basic amino acid obtained by removing a terminal amino group of the basic amino acid having two or more amino group on the terminal of the amino acid. Examples of the above-described basic amino acid having two or more amino group on the terminal of the amino acid include lysine, arginine, hydroxylysine and the like. $R^9$ represents a residual group of an amino acid other than $R^8$, and examples of such amino acid include glutamic acid, aspartic acid, alanine, serine, threonine, valine, methionine, leucine, isoleucine, tyrosine, phenylalanine, proline, hydroxyproline and the like.

Examples of the amino acid compositions of typical proteins which are used as a starting material of the peptide represented by B in the formula (I) are as shown in the following Tables 1 and 2.

TABLE 1

| | Amino acid composition (mol %) | | |
|---|---|---|---|
| | Collagen | Keratin | Wheat |
| Glycine | 35.4 | 8.8 | 6.8 |
| alanine | 11.2 | 6.0 | 4.2 |
| valine | 2.1 | 6.2 | 2.7 |
| leucine | 2.4 | 7.6 | 6.5 |
| isoleucine | 1.0 | 2.8 | 1.6 |
| phenylalanine | 1.4 | 1.7 | 4.5 |
| tyrosine | 13.4 | 8.4 | 14.4 |
| threonine | 0.8 | 9.0 | 2.1 |
| serine | 1.9 | 10.8 | 6.1 |
| tyrosine | 0.3 | 1.5 | 1.5 |
| methionine | 0.6 | 0.1 | 1.4 |
| halfcystine | — | 10.2 | 2.2 |
| arginine | 9.8 | 9.8 | 0.1 |
| histidine | 0.4 | 0.7 | 2.2 |
| lysine | 2.7 | 3.3 | 1.1 |
| aspartic acid | 4.7 | 3.6 | 3.0 |
| glutamic acid | 7.8 | 9.5 | 39.6 |
| hydroxyproline | 9.3 | — | — |
| hydroxylysine | 0.9 | — | — |

TABLE 2

| | Amino acid composition (mol %) | | |
|---|---|---|---|
| | Soybean | Silk | Yeast |
| Glycine | 9.5 | 42.9 | 8.2 |
| alanine | 7.2 | 30.6 | 9.4 |
| valine | 5.2 | 2.6 | 7.7 |
| leucine | 7.9 | 0.6 | 9.0 |
| isoleucine | 3.8 | 1.0 | 5.9 |
| phenylalanine | 3.5 | 2.3 | 4.2 |
| tyrosine | 7.2 | 0.3 | 3.0 |
| threonine | 1.2 | 0.9 | 5.9 |
| serine | 3.2 | 9.7 | 5.7 |
| tyrosine | 1.6 | 4.9 | 3.2 |
| methionine | 1.0 | trace | 1.3 |
| halfcystine | 0.3 | trace | 0.5 |
| arginine | 1.6 | 0.1 | 4.7 |
| histidine | 3.5 | trace | 2.1 |
| lysine | 4.4 | 0.5 | 7.7 |
| aspartic acid | 15.3 | 2.1 | 10.1 |
| glutamic acid | 23.6 | 1.5 | 11.4 |
| hydroxyproline | — | — | — |
| hydroxylysine | — | — | — |

In the silylated peptide of the formula (VII), q is from 0 to 500, preferably more than 0 and not more than 200, more preferably more than 0 and not more than 50, particularly preferably more than 0 and not more than 10; r is from 0 to 500, preferably more than 0 and not more than 200, more preferably from 1 to 100, particularly preferably from 2 to 40; and q+r is from 1to 500, preferably from 1 to 200, more preferably from 2 to 100, particularly preferably from 3 to 50.

When q exceeds the above-described range, adsorbability onto hair as a peptide decreases. When r exceeds the above-described range, the number of the silyl functional group connected to an amino group is the side chain increases, the ratio of the silyl functional group part to the peptide part lowers, consequently, properties owned by the silyl functional group part can not be fully manifested. When q+r exceeds the above-described range, permeability and adsorbability onto hair as a peptide decreases as compared with a peptide having lower molecular weight, and further, it tends to coagulate in storage and storage stability thereof decreases. q, r and q+r represent theoretically an integer, however, when the peptide part is a hydrolyzed peptide as described below, measured values will be the averaged and may not be an integer since the hydrolyzed peptide is obtained in the form of a mixture of compounds having different molecular weights.

Peptides used as the above-described silylated peptide represented by the general formula (VII) include amino acids, peptides, and esters of amino acids or peptides. Examples of the above-described amino acid include alanine, glycine, valine, leucine, isoleucine, proline, phenylalanine, tyrosine, serine, threonine, methionine, arginine, histidine, lysine, asparagine, aspartic acid, glutamine, glutamic acid, cystine, cysteine, cysteic acid, tryptophan, hydroxyproline, hydroxylysine, o-phophoserine, citrulline and the like.

Examples of the above-described peptide include natural peptides, synthetic peptides, hydrolyzed peptides obtained by partial hydrolysis of proteins using an acid, alkali, enzyme or combination thereof.

Examples of the natural peptide include glutathione, bacitracin A, insulin, glucagon, oxytocin, basopressin and the like, and examples of the synthetic peptide include polyglycine, polylysine, polyglutamic acid, polyserine and the like.

Examples of the hydrolyzed peptide include peptides obtained by partial hydrolysis, using an acid, alkali, enzyme or combination thereof, of proteins derived from animal and vegetable such as collagen (including gelatin which is denatured substance thereof), keratin, silk fibroin, sericin, casein, conchiolin, elastin; yolk protein and albumen protein of eggs of chicken, duck and the like; soybean protein, wheat protein, corn protein, rice (rice bran) protein, potato protein and the like, or proteins derived from microorganisms such as yeast proteins separated from yeasts of Sacchamomyces, Candida and Endomycopsis and yeasts called beer yeast and sake yeast, proteins extracted from mushrooms (spore yeast), proteins separated from chlorella, and the like.

As the esters of the above-described amino acids or peptides, carboxyl esters with hydrocarbon alcohol having 1 to 20 carbon atoms, such as a methyl ester, ethyl ester, propyl ester, isopropyl ester, lauryl ester, cetyl ester, 2-ethylhexyl ester, 2-hexyldecyl ester, stearyl ester and the like, are exemplified.

The one or more silane compounds(III) represented by the general formula (III) is usually obtained by hydrolyzing a silane compound represented by the following general formula (II):

$$R^2_n SiX_{(4-n)} \tag{II}$$

wherein n represents an integer from 0 to 2, $R^2$ represents an organic group in which a carbon atom is directly connected to the silicon atom and when n is 2, the two $R^2$ groups may be the same or different, and X represent at least one group selected from the group consisting of a hydroxyl group, alkoxy group, halogen group, carboxyl group and amino group and the two or more X groups may be the same or different.

By hydrolysis, a silane compound represented by the general formula (II) generates at least two hydroxyl groups directly connected to a silicon atom and becomes a silane compound represented by the genera formula (III) to be polycondensed with the organic silane compound having a hydrophilic group represented by the general formula (I). Specific examples of such a silane compound represented by the general formula (II) include tetramethoxysilane, methyltrimethoxysilane, methyldimethoxysilane, dimethyldimethoxysilane, phenyltrimethoxysilane, diphenyldimethoxysilane, hexyltrimethoxysilane, decyltrimethoxysilane, vinyltrimethoxysilane, 3-methacryloxypropyltrimethoxysilane, 3-methacryloxypropylmethyldimethoxysilane, N-(2-aminoethyl)-3-aminopropyltrimethoxysilane, N-(2-aminoethyl)-3-aminopropylmethyldimethoxysilane, 3-aminopropyltrimethoxysilane, N-phenyl-3-aminopropyltrimethoxysilane, 3-chloropropyltrimethoxysilane, 3-chloropropylmethyldimethoxysilane, 3-mercaptopropyltrimethoxysilane, 3-glycosidoxypropyltrimethoxysilane, 3-glycosidoxypropylmethyldimethoxysilane, dimethyloctadecyl[3-(trimethoxysilyl)propyl]ammonium chloride, 3-(trimethoxysilyl)propylpolyoxyethylene (10) ether, tetraethoxysilane, methyltriethoxysilane, methyldiethoxysilane, dimethyldiethoxysilane, phenyltriethoxysilane, diphenyldiethoxysilane, vinyltriethoxysilane, 3-methacryloxypropyltriethoxysilane, 3-methacryloxypropylmethyldiethoxysilane, N-(2-aminoethyl)-3-aminopropyltriethoxysilane, N-(2-aminoethyl)-3-aminopropylmethyldiethoxysilane, 3-aminopropyltriethoxysilane, 3-chloropropyltriethoxysilane, 3-chloropropylmethyldiethoxysilane, 3-glycosidoxypropylmethyldiethoxysilane, 3 -isocyanatepropyltriethoxysilane, methyldichlorosilane, methyltrichlorosilane, dimethyldichlorosilane, phenyltrichlorosilane, diphenyldichlorosilane, vinyltrichlorosilane, 3-chloropropylmethyldichlorosilane and the like, and compounds obtained by condensing protein, alkyl group, polyoxyethylene ether, polyoxypropylene ether, acrylic polymer, polyester, resin acid, dye, ultraviolet ray absorber, preservatives, sterilizer, alkylammonium, aromatic ring and the like with a silane coupling agent such as N-(2-aminoethyl)-3-aminopropyltrimethoxysilane, N-(2-aminoethyl)-3-aminopropylmethyldimethoxysilane, 3-aminopropyltrimethoxysilane, 3-chloropropyltrimethoxysilane, 3-chloropropylmethyldimethoxysilane, 3-mercaptopropyltrimethoxysilane, 3-glycosidoxypropyltrimethoxysilane, 3-glycosidoxypropylmethyldimethoxysilane, 3-methacryloxypropyltriethoxysilane, 3-methacryloxypropylmethyldiethoxysilane, N-(2-aminoethyl)-3-aminopropyltriethoxysilane, N-(2-aminoethyl)-3-aminopropylmethyldiethoxysilane, 3-aminopropyltriethoxysilane, 3-chloropropyltriethoxysilane, 3-chloropropylmethyldiethoxysilane, 3-glycosidoxypropylmethyldiethoxysilane, 3-isocyanate propyltriethoxysilane and the like.

As the silane compound represented by the general formula (II), commercially available silane compounds may also be used. Examples of the commercially available silane compounds include K B M 0 4, K B M 1 3, K B M 2 2, K B M 1 0 3, K B M 2 0 2, K B M 3 0 6 3, K B M 3 1 0 3, K B M 1 0 0 3, K B M 5 0 3, K B M 5 0 2, K B M 6 0 3, K B M 6 0 2, K B M 9 0 3, K B M 5 7 3, K B M 7 0 3, K B M 8 0 3, K B M 4 0 3, P O L O N M F 5 0, K B M 6 4 1, K B E 0 4, K B E 1 3, K B E 2 2, K B E 1 0 3, K B E 1 0 0 3, K B E 5 0 2, K B E 5 0 3, K B E 6 0 3, K B E 6 0 2, K B E 9 0 3, K B E 4 0 2, K A 1 2, K A 1 3, K A 2 2, K A 1 0 3, K A 2 0 2, K A 1 0 0 3 (trade name, manufactured by Shin-etsu silicone, Co., Ltd.), and T S L 8 1 1 3, T S L 8 1 1 7, T S L 8 1 1 2, T S L 8 1 7 3, T S L 8 1 7 2, T S I L 8 3 1 0, T S L 8 3 7 0, T S L 8 3 7 5, T S L 8 3 4 0, T S L 8 3 4 5, T S L 8 3 8 0, T S L 8 3 5 5, T S L 8 3 2 5, T S L 8 1 2 7, T S L 8 1 2 2, T S L 8 1 7 8, T S L 8 1 7 7, T S L 8 3 1 1, T S L 8 3 8 0, T S L 8 3 3 1, T S L 8 3 2 6, T S L 8 0 3 7, T S L 8 2 2 6, T S L 8 0 3 2, T S L 8 0 6 3, T S L 8 0 6 2, T S L 8 3 9 5 (trade name, manufactured by Toshiba silicone, Co., Ltd.), and S Z 6 0 7 0, S Z 6 3 0 0, S H 6 0 2 0, S Z 6 0 2 3, S H 6 0 6 2, S H 4 0 6 0, A Y 4 3-0 2 1, S Z 6 0 7 2, S Z 6 0 3 0, P R X 1 1, P R X 1 9 (trade name, manufactured by Toray-Dow Corning silicone, Co., Ltd.) and A -1 8 9, A - 1 8 6, A - 1 8 7, A - 1 3 1 0 (trade name, manufactured by Nippon Unikar, Co., Ltd.).

In the reaction of an organic silane compound having a hydrophilic group represented by the general formula (I) with a silyl compound represented by the general formula (III), for example, an aqueous solution of the organic silane compound having a hydrophilic group represented by the general formula (I) is controlled to become acidic with hydrochloric acid, sulfuric acid or the like, or controlled to become basic with an aqueous sodium hydroxide solution, an aqueous potassium hydroxide solution or the like, and then, the silane compound represented by the general formula (II) is added dropwise to this solution. By this procedure, an alkoxy group, a halogen group and the like of the silane compound represented by the general formula (II) are hydrolyzed to give a silane compound represented by the general formula (III) having at least two hydroxyl groups directly connected to a silicon atom, then, by conducting neutralization, a hydroxyl group of the organic silane compound having a hydrophilic group represented by the general formula (I) is polycondensed with a hydroxyl group of the silane compound represented by the general formula (III) to obtain an silane copolymer(T). In the above reaction, hydrolysis of the silane compound represented by the general formula (II) into the silane compound represented by the general formula (III) is effected in the same system in which polycondensation with the organic silane compound represented by the general formula (I) is conducted, and there is no need to conduct the hydrolysis of the silane compound represented by the general formula (II) in a system separated from the above-described polycondensation system.

When a silane compound represented by the general formula (VI) is used for producing the silane compound represented by the general formula (I), an aqueous solution of the silane compound represented by the general formula (VI) is controlled to become acidic with hydrochloric acid, sulfuric acid or the like, or controlled to become basic with an aqueous sodium hydroxide solution, an aqueous potassium hydroxide solution or the like so that an alkoxy group or a halogen group connected to the silyl group in the compound (VI) causes hydrolysis to give a hydroxyl group and the organic silane compound represented by the general formula (I) is formed. Therefore, the silane compound represented by the general formula (II) is thereafter added dropwise into the solution as described above to cause hydrolysis of an alkoxy group, a halogen group or the like of the silane compound represented by the general formula (II) for forming the silane compound represented by the general formula (III), then, by conducting neutralization, a hydroxyl group of the organic silane compound (I) having a hydrophilic group is polycondensed with a hydroxyl group of the silane compound represented by the general formula (III) to give a silane copolymer. Also when the silane compound represented by the general formula (VI) is used, hydrolysis thereof can be conducted by controlling to acidic pH or basic pH as described above, therefore, hydrolysis of the silane compound represented by the general formula (VI) into the silane compound represented by the general formula (I) can also be effected in the same system as the reaction system for polycondensing the above-described organic silane compound (I) with the silane compound represented by the general formula (III) and is not required to be conducted in a separate system.

The hydrolysis reaction generally proceeds at pH 2 to 3. However, when certain kinds of organic silane compound represented by the general formula (I) is used, insoluble materials tend to be formed on acidic pH. Therefore, the hydrolysis is preferably conducted at pH 10 to 11 in these cases. When an alkoxysilane compound is used as the silane compound represented by the general formula (II), pH control is required only before dropwise addition of the alkoxysilane compound. However, when a halogenated silane compound or carboxysilane compound is used as the silane compound represented by the general formula (II) and the reaction is conducted on basic pH, it is necessary to keep pH between 10 and 11 by adding an aqueous sodium hydroxide solution, an aqueous potassium hydroxide solution or the like, since pH lowers during the reaction. Further, when an amino silane compound is used as the silane compound represented by the general formula (II) and the reaction is conducted on acidic pH, it is necessary to keep pH between 2 and 3 by adding diluted hydrochloric acid, diluted sulfuric acid or the like, since pH increases during the reaction.

The reaction temperature is preferably from 30 to 60° C. When the reaction temperature is too low, the reaction does not proceed easily and when the reaction temperature is too high an alkoxy group or a halogen group of a silane compound represented by the general formula (III) is hydrolyzed steeply. It is preferable to add a silane compound represented by the general formula (II) dropwise over 30 minutes to 2 hours, and then, the mixture is stirred for 1 to 6 hours, though it varies depending on reaction amount.

On completion of the hydrolysis reaction, a silane compound represented by the general formula (I) and a silane compound represented by the general formula (III) are dissociated since the reaction solution is acidic or basic. When the reaction solution is acidic, an aqueous alkali solution such as an aqueous sodium hydroxide solution, aqueous potassium hydroxide solution or the like is added, and when the reaction solution is basic, an acid aqueous solution such as dilute hydrochloric acid, dilute sulfuric acid or the like is added, and the solution is stirred for neutralization. By this neutralization, polycondensation proceeds to give an organic silane copolymer. Stirring after the neutralization is preferably conducted for 2 to 10 hours.

Then, one or more silane compounds represented by the general formula (V) is reacted with the organic silane copolymer obtained as described above.

The one or more silane compounds represented by the general formula (V) is usually obtained by hydrolysis of a silane compound represented by the following general formula (IV):

$$R^3{}_3SiZ \qquad (IV)$$

wherein, $R^3$ represent an organic group in which a carbon atom is directly connected to the silicon atom and the three $R^3$ groups may be same or different, and Z represents at least one group selected from the group consisting of a hydroxyl group, alkoxy group, halogen group, carboxyl group and amino group.

Examples of the silane compound represented by the general formula (IV) include dimethylvinylchlorosilane, n-butyldimethylchlorosilane, tert-butyldimethylchlorosilane, tert-butyldiphenylchlorosilane, octadecyldimethylchlorosilane, methyldiphenylchlorosilane, tri-n-butyldimethylchlorosilane, triethylchlorosilane, trimethylchlorosilane, tri-n-propylchlorosilane, triphenylchlorosilane, trimethylsilyliodide, dimethylethoxysilane, dimethylvinylethoxysilane, dimethylvinylmethoxysilane, trimethylethoxysilane, trimethylmethoxysilane, triphenylethoxysilane and the like.

In addition, silyl compounds having two silicon atoms such as hexamethyldisilazane and hexamethyldisiloxane can also be used since in these compounds, one hydroxyl group directly connected to a silicon atom is generated by hydrolysis.

As the silane compound represented by the general formula (IV), commercially available silane compounds may also be used. Examples of the commercially available silane compounds include T S L 8 3 0 5, T S L 8 2 1 6, T S L 8 2 1 7, T S L 8 2 1 8, T S L 8 0 8 0, T S L 8 0 6 6, T S L 8 2 5 3, T S L 8 2 5 8, T S L 8 0 3 1, T S L 8 2 5 4, T S L 8 0 6 1, T S L 8 2 6 8, T S L 8 1 2 6, T S L 8 3 1 8, T S L 8 3 1 7, T S L 8 1 2 1, T S L 8 1 1 1, T S L 8 2 6 9, T S L 8 8

2 0, T S L 8 2 3 8 (tradename, manufactured by Toshiba silicone, Co., Ltd.), and P R X 2 4, S Z 6 0 7 9 (trade name, manufactured by Toray-Dow Corning silicone, Co., Ltd.).

Since a silane compound of the formula (IV) has only one reactive group directly connected to a silicon atom, a silane compound of the formula (V) obtained by hydrolysis of the silane compound of the formula (IV) has only one hydroxyl group, which is reacted with a hydroxyl group existing in the organic silane copolymer to reduce the number of a hydroxyl group in the silane copolymer and to prevent further polycondensation of the silane copolymer. Namely, by reacting the silane compound represented by the general formula (V) obtained by hydrolysis of the silane compound represented by the general formula (IV), a silane copolymer having excellent storage stability can be obtained. Further, the molecular weight of the silane copolymer can be controlled by allowing a silane compound represented by the general formula (V) to react during polycondensation reaction by neutralization of an organic silane compound represented by the general formula (I) with a silane compound represented by the general formula (III).

For example, by adding dropwise the silane compound represented by the general formula (V) to an aqueous solution of the organic silane copolymer, a hydroxyl group of the silane compound represented by the general formula (V) is condensed with a hydroxyl group in the organic silane copolymer as shown in the following reaction formula.

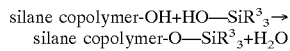

silane copolymer-OH+HO—SiR$^3_3$→
silane copolymer-O—SiR$^3_3$+H$_2$O

Among silane compounds represented by the general formula (IV), a silane compound in which Z represents a halogen atom shows excellent hydrolysis property, therefore, even if this silane compound represented by the general formula (IV) is directly added to an aqueous solution of an organic silane copolymer dropwise, the halogen atom is easily hydrolyzed and the above-described reaction progresses. However, when a silane compound of the general formula (IV) in which Z represents an alkoxy group or a silane compound containing two silicon atoms such as hexamethyldisiloxane is used, it is necessary that hydrolysis is previously conducted in an aqueous solution having pH 2 to 3 to give a silane compound represented by the general formula (V) and then this silane compound is added to an aqueous solution of an organic silane copolymer dropwise.

The reaction temperature of an organic silane copolymer with a silane compound represented by the general formula (V) is preferably from 30 to 60° C. It is preferable to add a silane compound represented by the general formula (V) dropwise over 30 minutes to 2 hours, and then, the mixture is stirred for 1 to 6 hours, though it varies depending on reaction amount.

After completion of the stirring, the reaction solution is neutralized with an aqueous alkali solution such as an aqueous sodium hydroxide solution, an aqueous potassium hydroxide solution or the like, and the reaction is completed by further stirring for 2 to 10 hours, to obtain a silane copolymer.

The silane copolymer obtained by the above-described reaction is represented by the following rational formula:

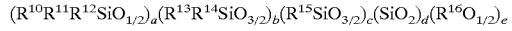

$(R^{10}R^{11}R^{12}SiO_{1/2})_a(R^{13}R^{14}SiO_{3/2})_b(R^{15}SiO_{3/2})_c(SiO_2)_d(R^{16}O_{1/2})_e$ wherein, $R^{10}$ to $R^{15}$, which are same or different, represent an organic group in which a carbon atom is directly connected to a silicon atom, provided that at least one of $R^{13}$ to $R^{15}$ represents a —A—B group in the formula (I), the remaining groups represent $R^1$ or $R^2$ in the formula (I) or (III), respectively, for example, a hydrogen atom, an alkyl group having 1 to 18 carbon atoms or a phenyl group, $R^{16}$ represents a hydrogen atom or a lower alkyl group, and a is an integer of 0 or more, b, c, d, e are an integer of 0 or more, b+c+d≧2, b+c≧1 and 1≦a+e≦c+2d+2.

Various properties of the silane copolymer can be obtained by changing the amount and kind of a silane compound in reaction.

For example, 1 mol or more of methyldiethoxysilane is polycondensed, as the silane compound represented by the general formula (II), per one mol of the organic silane compound represented by the general formula (I) in reaction, the obtained copolymer has strong silicone-like properties, and the stronger silicone-like properties can be obtained when more methyldiethoxysilane is polycondensed. When a compound having a hydrophilic group such as 3-(triemthoxysilyl)propylpolyoxyethylene ether and the like is used as the silane compound represented by the general formula (II) and this compound having a hydrophilic group is polycondensed with an organic silane compound represented by the general formula (I), the resulting silane copolymer has increased hydrophilicity and when this composition is compounded in cosmetics, the moisture retaining property thereof is increased. Further, when dimethyloctadecyl-(3-trimethoxysilylpropyl)ammonium chloride in which a quaternary ammonium salt is connected is used as the silane compound represented by the general formula (II) and this chloride is hydrolyzed and polycondensed with an organic silane compound represented by the general formula (I), properties of the higher alkyl quaternary ammonium salt such as remarkable increase in adsorbability onto hair and the like are added in addition to excellent properties of the organic silane compound represented by the general formula (I).

After completion of the above-described polymerization reaction, pH of the reaction solution is controlled. Then, after purified by an ion exchange resin, dialysis membrane, electrical dialysis, gel filtration, ultrafiltration and the like, if necessary, and as the resulting liquid or after processed into a powder, the reaction solution is used as a compounding agent into cosmetics, fiber treating agent and the like.

The silane copolymer of the present invention has excellent properties based on an organic silane compound having a hydrophilic group represented by the general formula (I) and excellent properties added based on a silane compound represented by the general formula (III). For example, when a silylated peptide is used as the organic silane compound represented by the general formula (I), the silane copolymer of the present invention has excellent properties based on the silicone compound and excellent properties based on the polypeptide together. When this is compounded in hair cosmetics and skin cosmetics, luster and moisture feeling are imparted to hair, combability is improved, branching of hair is prevented, luster and moisture feeling are imparted to skin, and smoothness is imparted to skin. Among other, when the composition is compounded in a washing agent such as shampoo and the like, foam generated has soft feeling, hair and skin after use thereof become smooth, and, based on functional groups added of the silane compound represented by the general formula (III), for example, improvement of moisture retaining property, improvement of adsorbability onto hair, improvement of water repelling property, ultraviolet ray absorbing ability, antimicrobial and sterilizing property, film forming property, thickening property and the like are imparted.

Further, when a silane compound represented by the general formula (V) obtained by hydrolysis of a silane compound represented by the general formula (IV) is added to a hydroxyl group of the organic silane copolymer, i.e. in case of silane copolymer (U), the possibility of further polycondensation of the copolymer during storage is lowered due to lowered amount of a free hydroxyl group, consequently, this silane copolymer (U) has excellent storage stability.

The following examples further illustrate the present invention, but do not limit the scope thereof. Before the examples, conditions of gel filtration analysis and measuring conditions of infrared ray absorption spectrum used in the examples will be described. In the following examples, % showing concentration of solutions and dispersions is % by weight.

[Gel Filtration Analysis]

Gel filtration analysis was conducted under the following conditions. Analysis results of each examples are shown in FIGS. 1 to 11, respectively. In these figures, results of the obtained copolymerized compositions are shown by solid lines, and results of raw material silylated peptides are shown by broken lines.

Analysis Column: TSKgel G3000PW (7.5 mm ID×30 cm) manufactured by Tosoh Corp
Eluent: 0.1% trifluoroacetic acid+45% acetonitrile
Elution speed: 0.3 ml/min
Detector: UV detector, 220 nm
Standard sample: Bovine serum albumin (MW 66,000)
Carbonic anhydrase (MW 29,000)
Cytochrome C (MW 12,400)
Aprotinin (MW 6,500)
Insulin (MW 5,700)
α-MSH (melanocyte stimulating hormone) (MW 1,665)
Bradykinin (MW 1,060)

[Infrared Ray Absorption Spectrum Analysis]

In infrared ray absorption spectrum analysis, FT-IR 8200 PC manufactured by Shimadzu Corp. (hereinafter, referred to as FT-IR) was used. When a sample is liquid, a cell for liquid was used, and when a sample is made into a powder by freeze-drying and the like, the measurement was conducted by the KBr tablet method.

EXAMPLE 1

100 g of a 30% aqueous solution of a silylated hydrolyzed collagen represented by the general formula (VII), wherein, $R^5=CH_3$, $R^6$ and $R^7=OH$, connecting moiety A is —$(CH_2)_3$ $OCH_2CH(OH)CH_2$—, average of q=1.1, average of r=14.9, and average of q+r =16 (number average molecular weight 1750, 0.017 mol), was charged into a 500 ml beaker, and pH thereof was controlled to 3 with dilute hydrochloric acid. 15.3 g of dimethyldiethoxysilane (0.086 mol, 5 equivalent per silylated hydrolyzed collagen) was added dropwise to the solution with stirring on a hot water bath at 40° C. over 1 hour. After completion of the addition, the stirring was continued for 5 hours at 40° C. Then, pH thereof was controlled to 7 with an aqueous sodium hydroxide solution, and the solution was stirred for 4 hours at 40° C. to conduct polycondensation.

After completion of the stirring, impurities were removed from the reaction solution by filtration, and the concentration was controlled to obtain 129 g of a 30% aqueous solution of a silane copolymer of a silylated hydrolyzed collagen and a silane compound.

The results of gel filtration analysis of the resulting silane copolymer and the raw material, silylated hydrolyzed collagen, are shown in FIG. 1. As apparent from FIG. 1, in the resulting silane copolymer, a peak corresponding to a gel filtration molecular weight of about 3600 of the raw material, silylated hydrolyzed collagen, nearly disappeared, and a large peak was recognized corresponding to a gel filtration molecular weight of about 13000. Namely, copolymerization of the silylated hydrolyzed collagen with the silane compound was recognized.

Parts of the resulting copolymer and the raw material, silylated hydrolyzed collagen, were respectively analyzed by FT-IR and the results were compared. A peak near 1250 $cm^{-1}$, which is believed to be derived from Si—$CH_3$ became stronger, and a peak near 1100 $cm^{-1}$, which is believed to be derived from Si—O was detected. Namely, it was recognized that the resulting silane copolymer has a Si—O—Si linkage.

EXAMPLE 2

100 g of a 30% aqueous solution of a silylated hydrolyzed collagen represented by the general formula (VII), wherein, $R^5=CH_3$, $R^6$ and $R^7=OH$, connecting moiety A is —$(CH_2)_3$ $OCH_2CH(OH)CH_2$—, average of q=1.1, average of r=14.9, and average of q+r=16 (number average molecular weight 1750, 0.017 mol), was charged into a 500 ml beaker, and pH thereof was controlled to 3 with dilute hydrochloric acid. 15.3 g of dimethyldiethoxysilane (0.086 mol, 5 equivalent per silylated hydrolyzed collagen) was added dropwise to the solution with stirring on a hot water bath at 40° C. over 1 hour. After completion of the addition, the stirring was continued for 5 hours at 40° C. Then, pH thereof was controlled to 7 with an aqueous sodium hydroxide solution, and the solution was stirred for 4 hours at 40° C. to conduct polycondensation. To this solution was added dropwise 3.7 g (0.034 mol) of trimethylchlorosilane over 30 minutes and the mixture was stirred. During this operation, pH of the solution was maintained from 7 to 8 by adding a 20% aqueous sodium hydroxide solution dropwise simultaneously. After completion of the addition, the mixture was further stirred for 3 hours to complete the reaction. After completion of the reaction, impurities were removed from the reaction solution by filtration, and the concentration was controlled to obtain 135 g of a 30% aqueous solution of a silane copolymer of a silylated hydrolyzed collagen and a silane compound.

Figure 2:
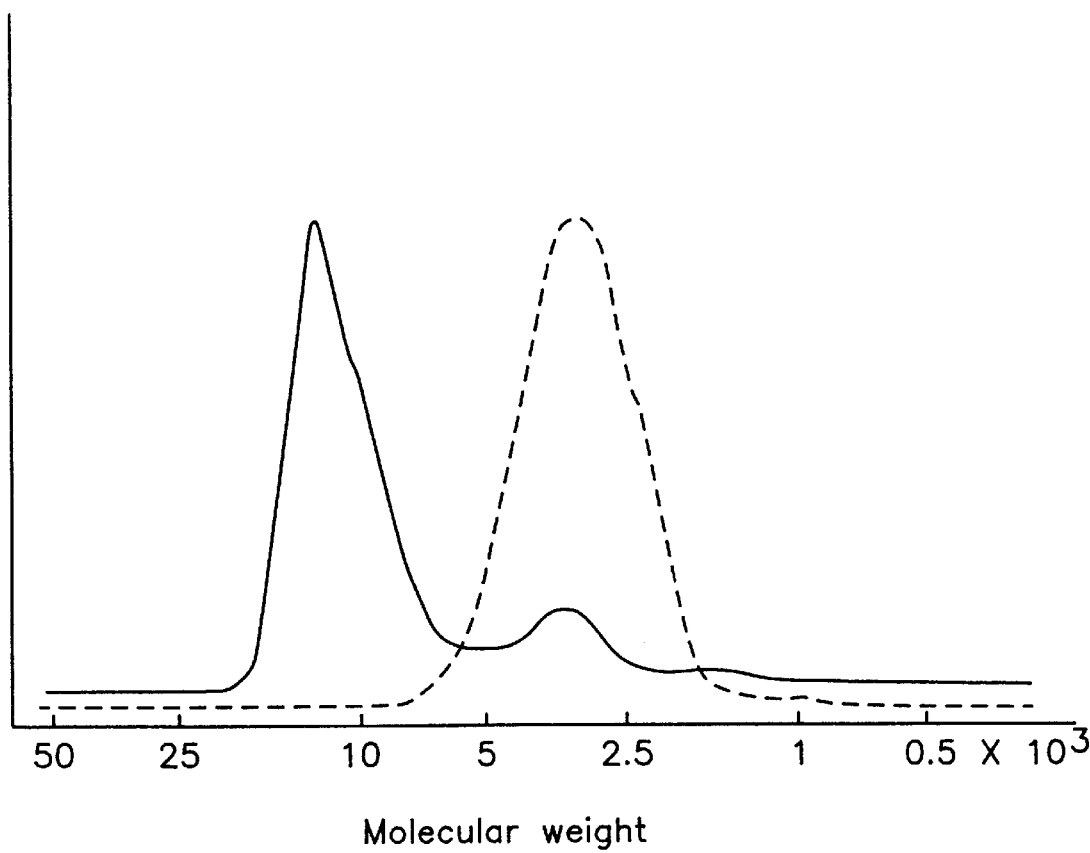
FIG. 2 is the results of gel filtration analysis of the silane copolymer obtained in Example 2 and the raw material used in Example 2.

The results of gel filtration analysis of the resulting silane copolymer and the raw material, silylated hydrolyzed collagen, are shown in FIG. 2. As apparent from FIG. 2, in the resulting silane copolymer, a peak corresponding to a gel filtration molecular weight of about 3600 of the raw material, silylated hydrolyzed collagen, nearly disappeared, and a large peak was recognized corresponding to a gel filtration molecular weight of about 12000. Namely, copolymerization of the silylated hydrolyzed collagen with the silane compound was recognized.

Parts of the resulting copolymer and the raw material, silylated hydrolyzed collagen, were respectively analyzed by FT-IR and the results were compared. A peak near 1250 $cm^{-1}$, which is believed to be derived from Si—$CH_3$ became stronger, and a peak near 1100 $cm^{-1}$, which is believed to be derived from Si—O was detected. Namely, it was recognized that the resulting silane copolymer has a Si—O—Si linkage.

EXAMPLE 3

Same procedure as in Example 1 was repeated except that 100 g of a 25% aqueous solution of a silylated hydrolyzed keratin represented by the general formula (VII), wherein, $R^5=CH_3$, $R^6$ and $R^7=OH$, connecting moiety A is —$(CH_2)_3$—, average of q=1, average of r=6, and average of q+r=7 (number average molecular weight 800, 0.03 mol), were used instead of the aqueous solution of a silylated hydrolyzed collagen and the amount of dimethyldiethoxysilane was changed to 8 g (0.06 mol. 2 equivalent per silylated hydrolyzed keratin) to obtain 88 g of a 20% aqueous solution of a silane copolymer of a silylated hydrolyzed keratin and a silane compound.

Figure 3:
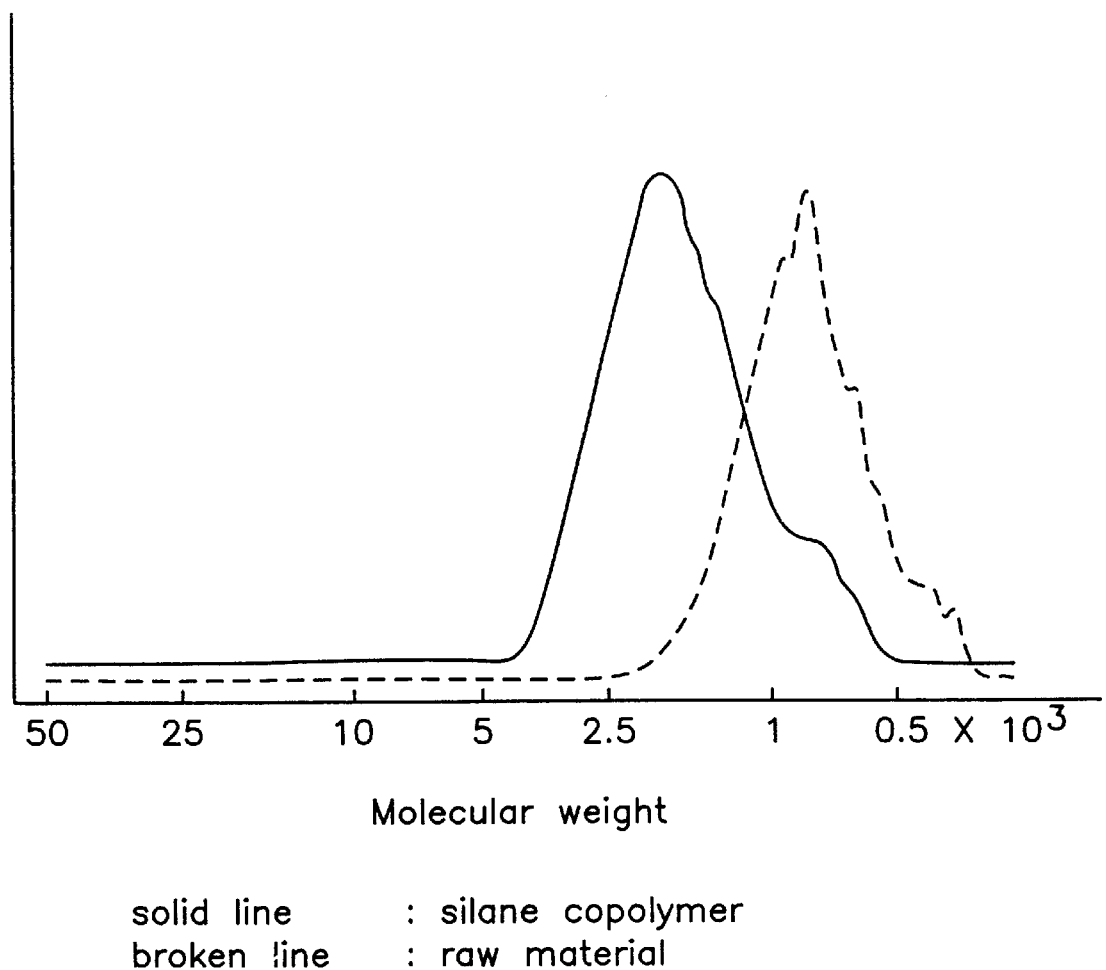
FIG. 3 is the results of gel filtration analysis of the silane copolymer obtained in Example 3 and the raw material used in Example 3.

The results of gel filtration analysis of the resulting silane copolymer and the raw material, silylated hydrolyzed keratin, are shown in FIG. 3. As apparent from FIG. 3, in the resulting silane copolymer, a peak corresponding to a gel filtration molecular weight of about 880 of the raw material, silylated hydrolyzed keratin, became weaker, and a peak was recognized corresponding to a gel filtration molecular weight of about 2500. Namely, copolymerization of the silylated hydrolyzed keratin with the silane compound was recognized.

Parts of the resulting copolymer and the raw material, silylated hydrolyzed keratin, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 4

Same procedure as in Example 2 was repeated except that 100 g of a 25% aqueous solution of a silylated hydrolyzed keratin represented by the general formula (VII), wherein, $R^5=CH_3$, $R^6$ and $R^7=OH$, connecting moiety A is —$(CH_2)_3$—, average of q=1, average of r=6, and average of q+r=7 (number average molecular weight 800, 0.03 mol), were used instead of the aqueous solution of a silylated hydrolyzed collagen and the amount of dimethyldiethoxysilane and trimethylchlorosilane were changed to 8 g (0.06 mol, 2 equivalent per silylated hydrolyzed keratin) and 6.5 g(0.06 mol), respectively to obtain 90 g of a 20% aqueous solution of a silane copolymer of a silylated hydrolyzed keratin and a silane compound.

Figure 4:
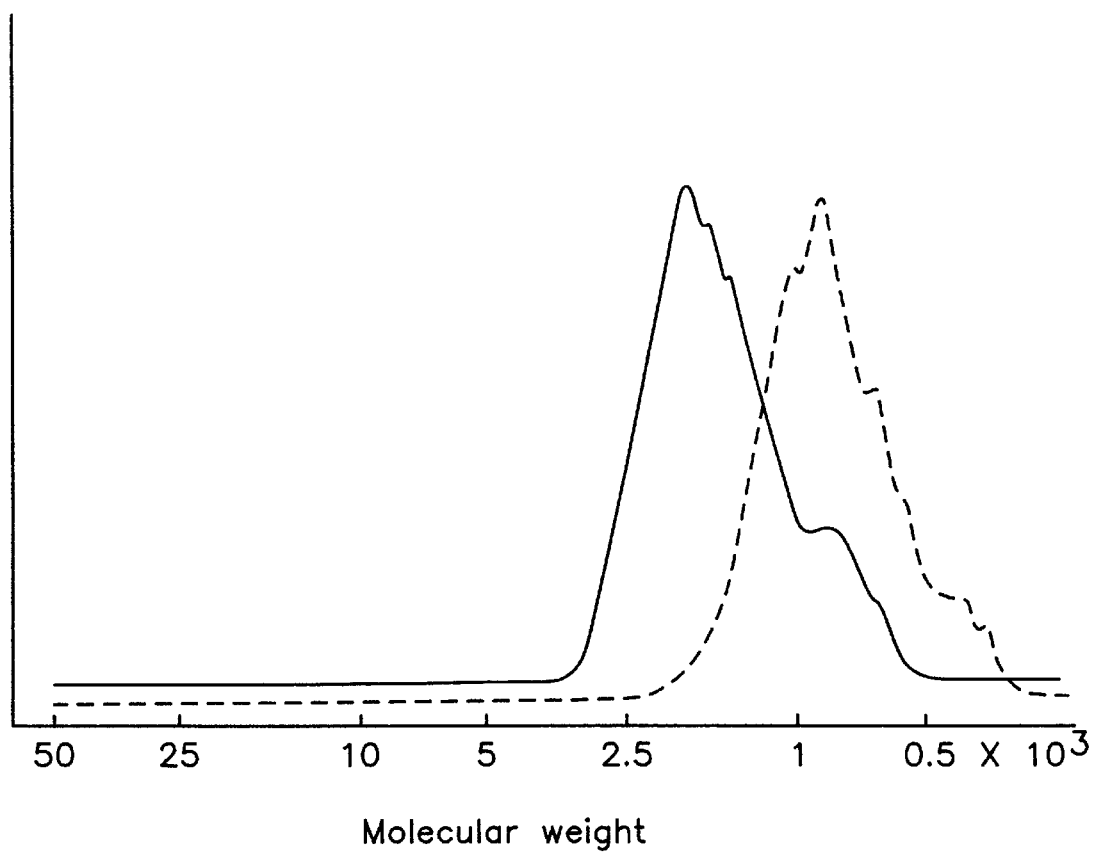
FIG. 4 is the results of gel filtration analysis of the silane copolymer obtained in Example 4 and the raw material used in Example 4.

The results of gel filtration analysis of the resulting silane copolymer and the raw material, silylated hydrolyzed keratin, are shown in FIG. 4. As apparent from FIG. 4, in the resulting silane copolymer, a peak corresponding to a gel filtration molecular weight of about 880 of the raw material, silylated hydrolyzed keratin, became weaker, and a peak was recognized corresponding to a gel filtration molecular weight of about 1800. Namely, copolymerization of the silylated hydrolyzed keratin with the silane compound was recognized.

Parts of the resulting copolymer and the raw material, silylated hydrolyzed keratin, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 5

100 g of a 30% aqueous solution of a silylated hydrolyzed wheat protein represented by the general formula (VII), wherein, $R^5=CH_3$, $R^6$ and $R^7=OH$, connecting moiety A is —$(CH_2)_3OCH_2CH(OH)CH_2$—, average of q=1, average of r=7, and average of q+r=8 (number average molecular weight 970, 0.03 mol), was charged into a 300 ml beaker, and pH thereof was controlled to 10.5 with an aqueous sodium hydroxide solution. 7.2 g of methyltriethoxysilane (0.04 mol. 1.3 equivalent per silylated hydrolyzed wheat protein) was added dropwise to the solution with stirring at 55° C. over 1.5 hour. After completion of the addition, the stirring was continued for 4.5 hours. Then, pH thereof was controlled to 6.5 with dilute hydrochloric acid, and the solution was stirred for 5 hours at 55° C. to conduct polycondensation.

After completion of the stirring, impurities were removed from the reaction solution by filtration, and the concentration was controlled to obtain 97 g of a 30% aqueous solution of a silane copolymer of a silylated hydrolyzed wheat protein and a silane compound.

Figure 5:
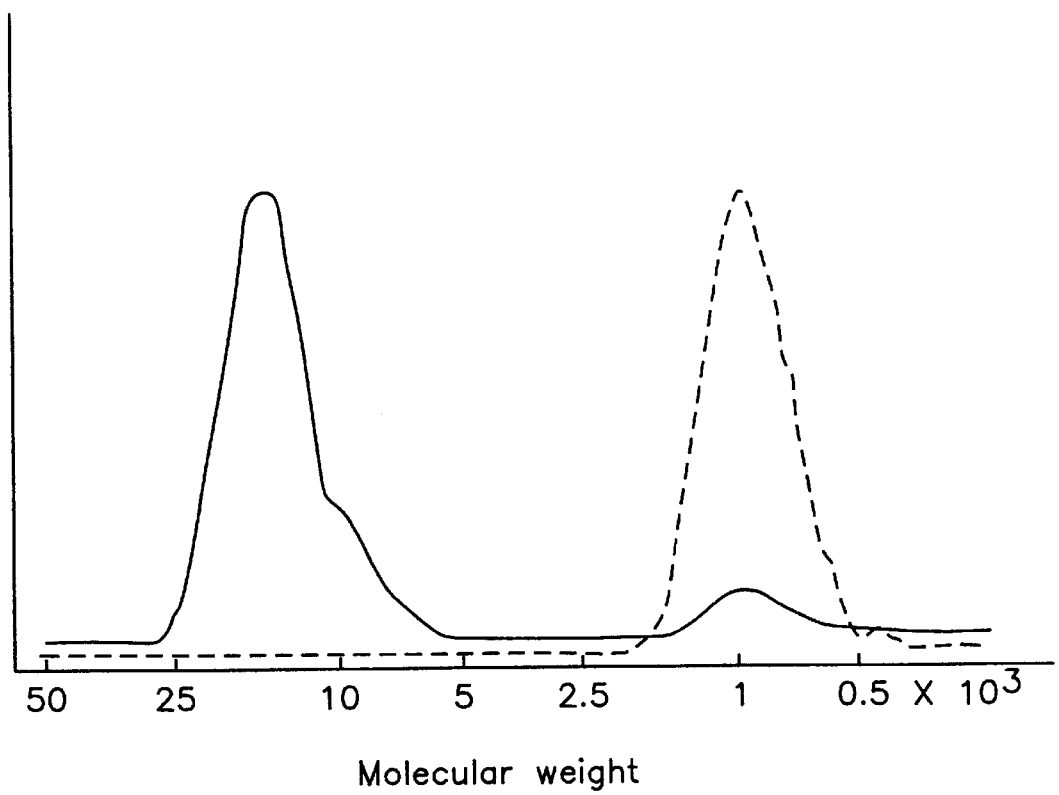
FIG. 5 is the results of gel filtration analysis of the silane copolymer obtained in Example 5 and the raw material used in Example 5.

The results of gel filtration analysis of the resulting silane copolymer and the raw material, silylated hydrolyzed wheat protein, are shown in FIG. 5. As apparent from FIG. 5, in the resulting silane copolymer, a peak corresponding to a gel filtration molecular weight of about 1000 of the raw material, silylated hydrolyzed wheat protein, became weaker, and a large peak was recognized corresponding to a gel filtration molecular weight of about 15000. Namely, formation of the copolymer was recognized.

Parts of the resulting copolymer and the raw material, silylated hydrolyzed wheat protein, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 6

100 g of a 25% aqueous solution of a silylated hydrolyzed soybean protein represented by the general formula (VII), wherein, $R^5$, $R^6$ and $R^7$ are OH, connecting moiety A is —$(CH_2)_3OCH_2CH(OH)CH_2$—, average of q=0.5, average of r=5.5, and average of q+r=6 (number average molecular weight 746, 0.034 mol), was charged into a 500 ml beaker, and pH thereof was controlled to 10.5 with an aqueous sodium hydroxide solution. 10 g of methyltrichlorosilane (0.068 mol, 2 equivalent per silylated hydrolyzed soybean protein) was added dropwise to the solution with stirring at 55° C. over 1.5 hour. During this operation, pH of the solution was maintained from 10 to 11 by adding an aqueous sodium hydroxide solution dropwise simultaneously. After completion of the addition, the stirring was continued for 5 hours. Then, pH thereof was controlled to 6.5 with dilute hydrochloric acid, and the solution was stirred for 5 hours at 55° C. to conduct polycondensation.

After completion of the stirring, the reaction solution was de-salted and purified by electrical dialysis, and the concentration was controlled to obtain 102 g of a 20% aqueous solution of a silane copolymer of a silylated hydrolyzed soybean protein and a silane compound.

Figure 6:
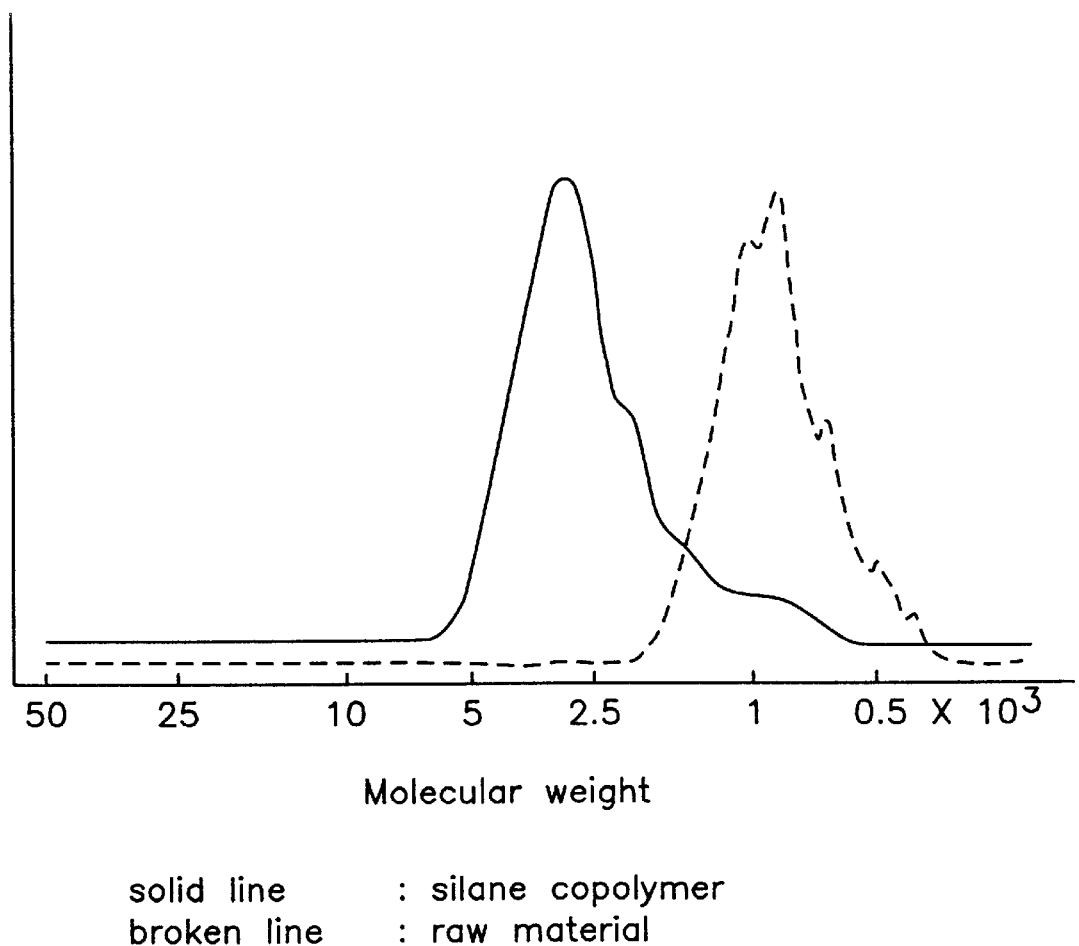
FIG. 6 is the results of gel filtration analysis of the silane copolymer obtained in Example 6 and the raw material used in Example 6.

The results of gel filtration analysis of the resulting silane copolymer and the raw material, silylated hydrolyzed soybean protein, are shown in FIG. 6. As apparent from FIG. 6, in the resulting silane copolymer, a peak corresponding to a gel filtration molecular weight of about 900 of the raw material, silylated hydrolyzed soybean protein, became weaker, and a large peak was recognized corresponding to a gel filtration molecular weight of about 3000. Namely, formation of the copolymer was recognized.

Parts of the resulting copolymer and the raw material, silylated hydrolyzed soybean protein, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 7

100 g of a 25% aqueous solution of a silylated hydrolyzed soybean protein represented by the general formula (VII), wherein, $R^5$, $R^6$ and $R^7$ are OH, connecting moiety A is —$(CH_2)_3OCH_2CH(OH)CH_2$—, average of q=0.5, average of r=5.5, and average of q+r=6 (number average molecular weight 746, 0.034 mol), was charged into a 500 ml beaker, and pH thereof was controlled to 10.5 with an aqueous sodium hydroxide solution. 10 g of methyltrichlorosilane (0.068 mol, 2 equivalent per silylated hydrolyzed soybean protein) was added dropwise to the solution with stirring at 55° C. over 1.5 hour. During this operation, pH of the solution was maintained from 10 to 11 by adding an aqueous sodium hydroxide solution dropwise simultaneously. After completion of the addition, the stirring was continued for 5 hours. Then, pH thereof was controlled to 6.5 with dilute hydrochloric acid, and the solution was stirred for 5 hours at 55° C. to conduct polycondensation.

To this solution was added dropwise 14.7 g (0.13 mol) of trimethylchlorosilane over 1 hour and the mixture was stirred. During this operation, pH of the solution was maintained from 7 to 8 by adding a 20% aqueous sodium hydroxide solution dropwise simultaneously. After completion of the addition, the mixture was further stirred for 3 hours to complete the reaction. After completion of the reaction, the reaction solution was de-salted and purified by electrical dialysis, and the concentration was controlled to obtain 102 g of a 20% aqueous solution of a silane copolymer of a silylated hydrolyzed soybean protein and a silane compound.

Figure 7:
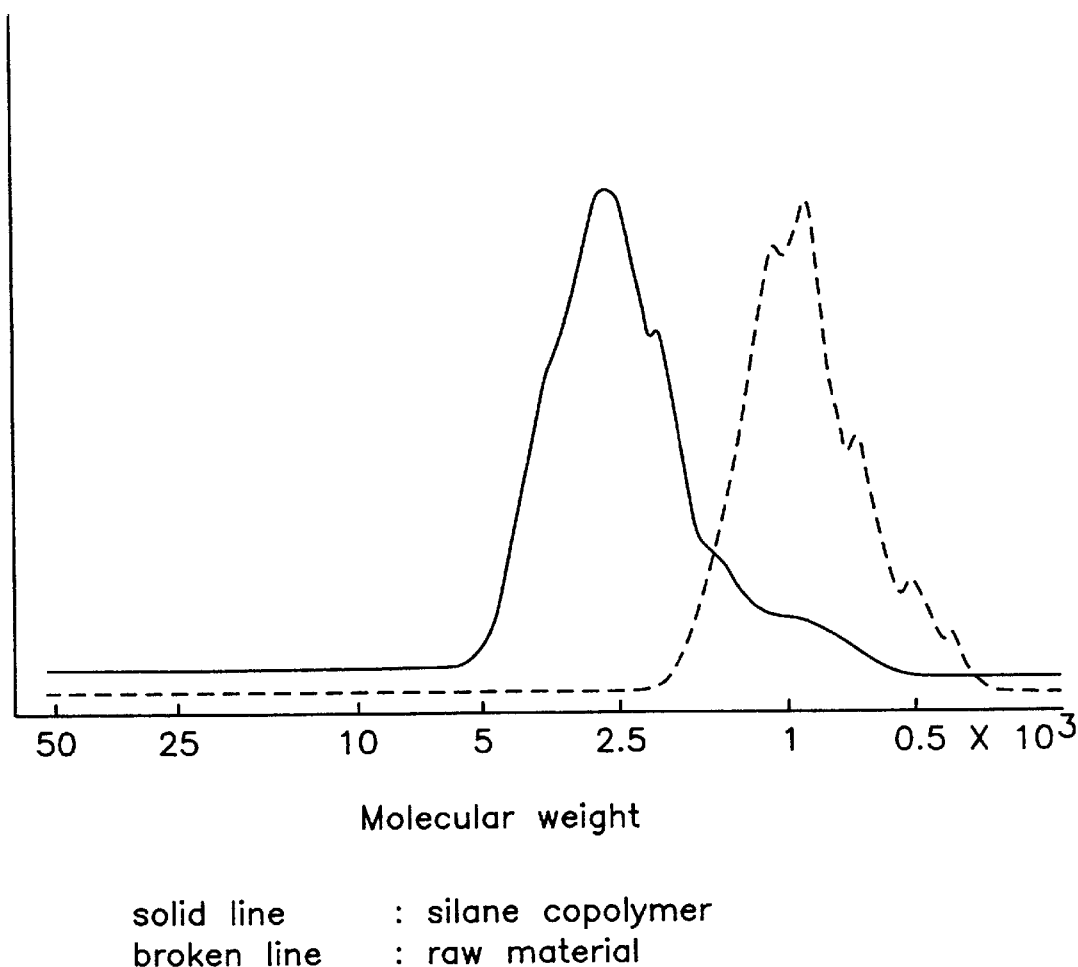
FIG. 7 is the results of gel filtration analysis of the silane copolymer obtained in Example 7 and the raw material used in Example 7.

The results of gel filtration analysis of the resulting silane copolymer and the raw material, silylated hydrolyzed soybean protein, are shown in FIG. 7. As apparent from FIG. 7, in the resulting silane copolymer, a peak corresponding to a gel filtration molecular weight of about 900 of the raw material, silylated hydrolyzed soybean protein, became weaker, and a large peak was recognized corresponding to a gel filtration molecular weight of about 2500. Namely, formation of the copolymer was recognized.

Parts of the resulting copolymer and the raw material, silylated hydrolyzed soybean protein, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 8

100 g of a 20% aqueous solution of a silylated hydrolyzed yeast protein represented by the general formula (VII), wherein, $R^5$, $R^6$ and $R^7$ are OH, connecting moiety A is —$(CH_2)_3OCH_2CH(OH)CH_2$—, average of q=1, average of r=4, and average of q+r=5 (number average molecular weight 600, 0.033 mol), was charged into a 500 ml beaker, and pH thereof was controlled to 10.5 with an aqueous sodium hydroxide solution. a mixture of 8.8 g of methyltriethoxysilane (0.066 mol, 2 equivalent per silylated hydrolyzed yeast protein) and 2 g of 3-(trimethoxysilyl)-propylpolyoxyethylene(10)ether (0.003 mol, 0.1 equivalent per silylated hydrolyzed yeast protein) was added dropwise to the solution with stirring at 50° C. over 1.5 hour. After completion of the addition, the stirring was continued at 50° C. for 5 hours. Then, pH thereof was controlled to 6.5 with dilute hydrochloric acid, and the solution was stirred for 6 hours at 50° C. to conduct polycondensation.

After completion of the stirring, impurities were removed from the reaction solution by filtration, and the concentration was controlled to obtain 102 g of a 20% aqueous solution of a silane copolymer of a silylated hydrolyzed yeast protein and a silane compound.

Figure 8:
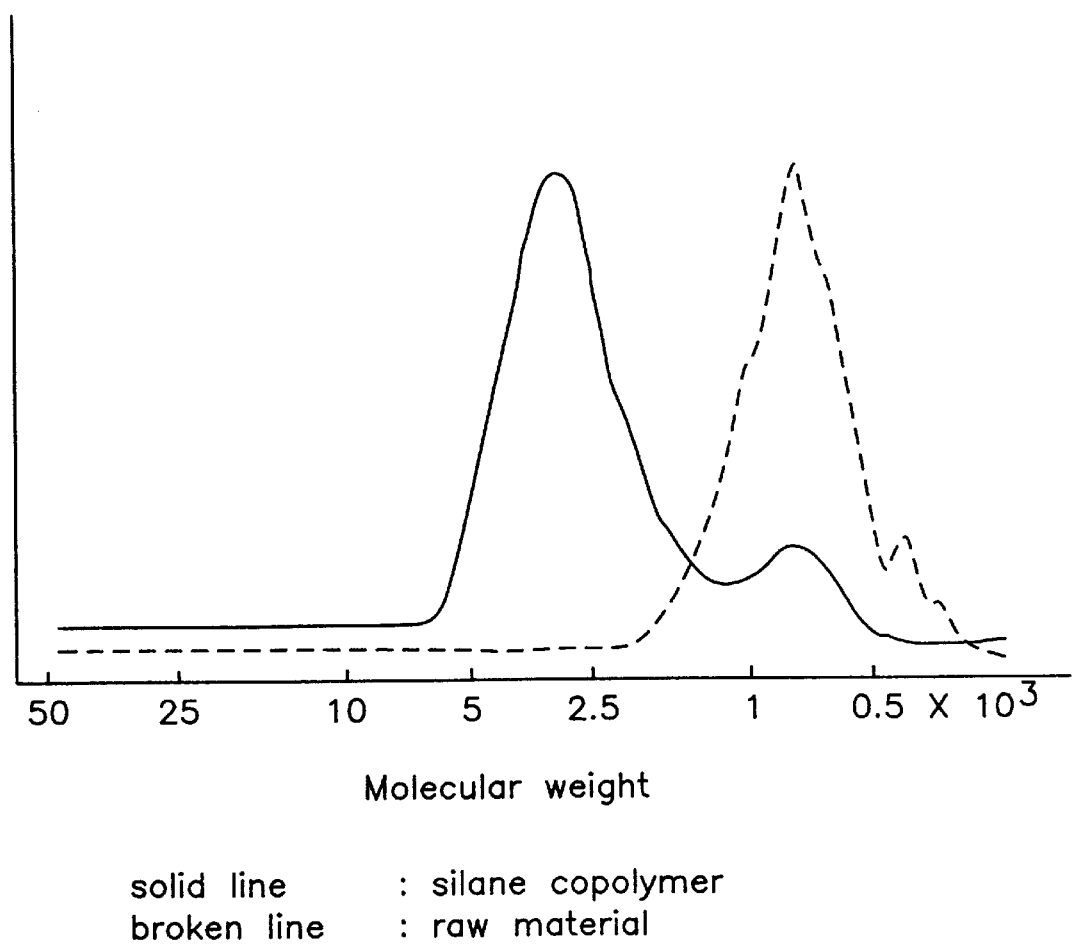
FIG. 8 is the results of gel filtration analysis of the silane copolymer obtained in Example 8 and the raw material used in Example 8.

The results of gel filtration analysis of the resulting silane copolymer and the raw material, silylated hydrolyzed yeast protein, are shown in FIG. 8. As apparent from FIG. 8, in the resulting silane copolymer, a peak corresponding to a gel filtration molecular weight of about 800 of the raw material, silylated hydrolyzed yeast protein, became weaker, and a large peak was recognized corresponding to a gel filtration molecular weight of about 3000. Namely, copolymerization of the silylated hydrolyzed yeast protein with the silane compound was recognized.

Parts of the resulting copolymer and the raw material, silylated hydrolyzed yeast protein, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 9

100 g of a 20% aqueous solution of a silylated hydrolyzed yeast protein represented by the general formula (VII), wherein, $R^5$, $R^6$ and $R^7$ are OH, connecting moiety A is —$(CH_2)_3OCH_2CH(OH)CH_2$—, average of q=1, average of r=4, and average of q+r=5 (number average molecular weight 600, 0.033 mol), was charged into a 500 ml beaker, and pH thereof was controlled to 10.5 with an aqueous sodium hydroxide solution. a mixture of 8.8 g of methyltriethoxysilane (0.066 mol, 2 equivalent per silylated hydrolyzed yeast protein) and 2 g of 3-(trimethoxysilyl)-propylpolyoxyethylene(10)ether (0.003 mol, 0.1 equivalent per silylated hydrolyzed yeast protein) was added dropwise to the solution with stirring at 50° C. over 1.5 hour. After completion of the addition, the stirring was continued at 50° C. for 5 hours. Then, pH thereof was controlled to 6.5 with dilute hydrochloric acid, and the solution was stirred for 6 hours at 50° C. to conduct polycondensation.

To this solution was added dropwise 15.1 g (0.14 mol) of trimethylchlorosilane over 1 hour and the mixture was stirred. During this operation, pH of the solution was maintained from 7 to 8 by adding a 20% aqueous sodium hydroxide solution dropwise simultaneously. After completion of the addition, the mixture was further stirred for 3 hours to complete the reaction.

After completion of the reaction, impurities were removed from the reaction solution by filtration, and the concentration was controlled to obtain 110 g of a 20% aqueous solution of a silane copolymer of a silylated hydrolyzed yeast protein and a silane compound.

Figure 9:
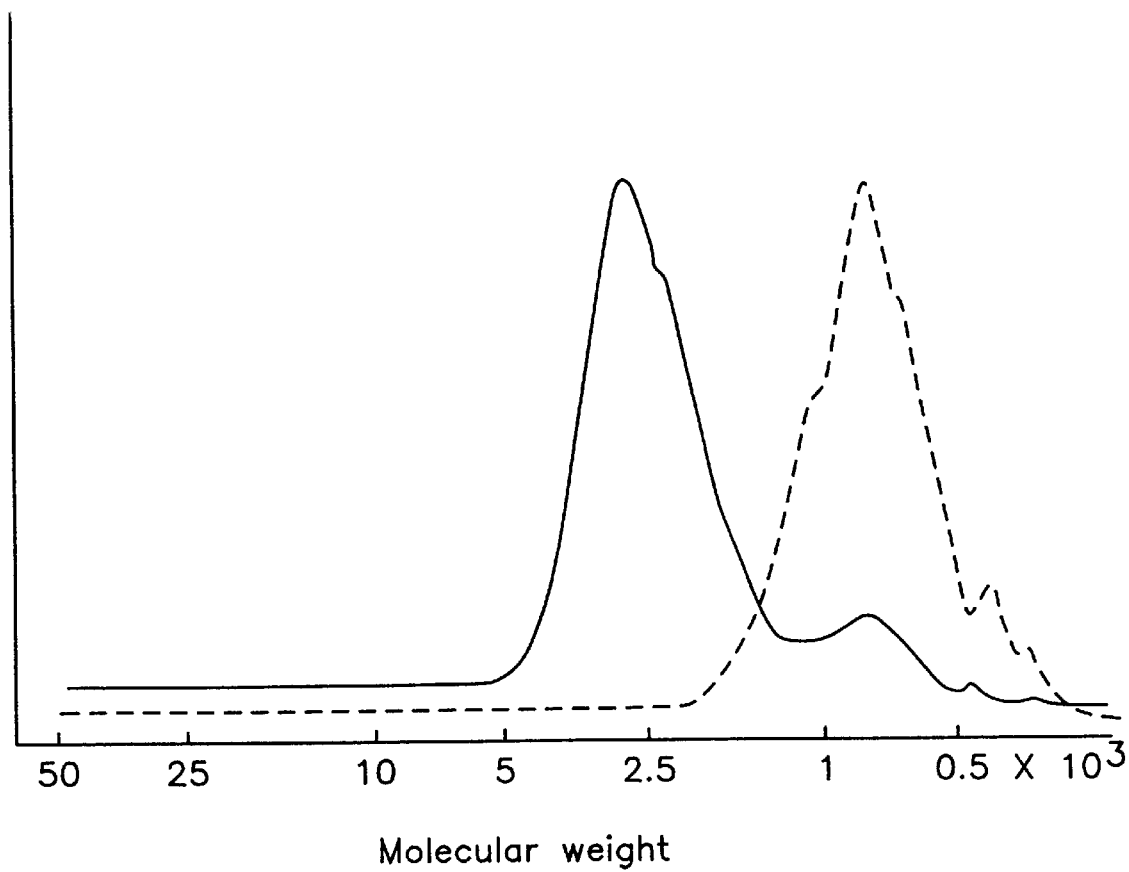
FIG. 9 is the results of gel filtration analysis of the silane copolymer obtained in Example 9 and the raw material used in Example 9.

The results of gel filtration analysis of the resulting silane copolymer and the raw material, silylated hydrolyzed yeast protein, are shown in FIG. 9. As apparent from FIG. 9, in the resulting silane copolymer, a peak corresponding to a gel filtration molecular weight of about 800 of the raw material, silylated hydrolyzed yeast protein, became weaker, and a large peak was recognized corresponding to a gel filtration molecular weight of about 2700. Namely, copolymerization of the silylated hydrolyzed yeast protein with the silane compound was recognized.

Parts of the resulting copolymer and the raw material, silylated hydrolyzed yeast protein, were respectively, analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 10

150 g of a 20% aqueous solution of a silylated hydrolyzed silk protein represented by the general formula (VII), wherein, $R^5=CH_3$, $R^6$ and $R^7=OH$, connecting moiety A is —$(CH_2)_3$—, average of q=0.06, average of r=9.94, and average of q+r=10 (number average molecular weight 1250, 0.024 mol), was charged into a 500 ml beaker, and pH thereof was controlled to 3 with dilute hydrochloric acid. A mixture of 6.4 g of dimethyldiethoxysilane (0.048 mol, 2 equivalent per silylated hydrolyzed silk protein) and 1.9 g of 50% ethanol solution of dimethyloctadecyl-[(3-trimethoxysilyl)-propyl]ammonium chloride (0.002 mol, 0.08 equivalent per silylated hydrolyzed silk protein) was added to the solution with stirring on a hot water bath at 50° C. over 1.5 hours. After completion of the addition, the stirring was continued for 5 hours at 50° C. Then, pH thereof was controlled to 7 with an aqueous sodium hydroxide solution, and the solution was stirred for 6 hours at 50° C. to conduct polycondensation.

After completion of the stirring, the concentration was controlled with 20% aqueous ethanol solution to obtain 193 g of a 10% aqueous solution of a silane copolymer of a silylated hydrolyzed silk protein and a silane compound.

Figure 10:
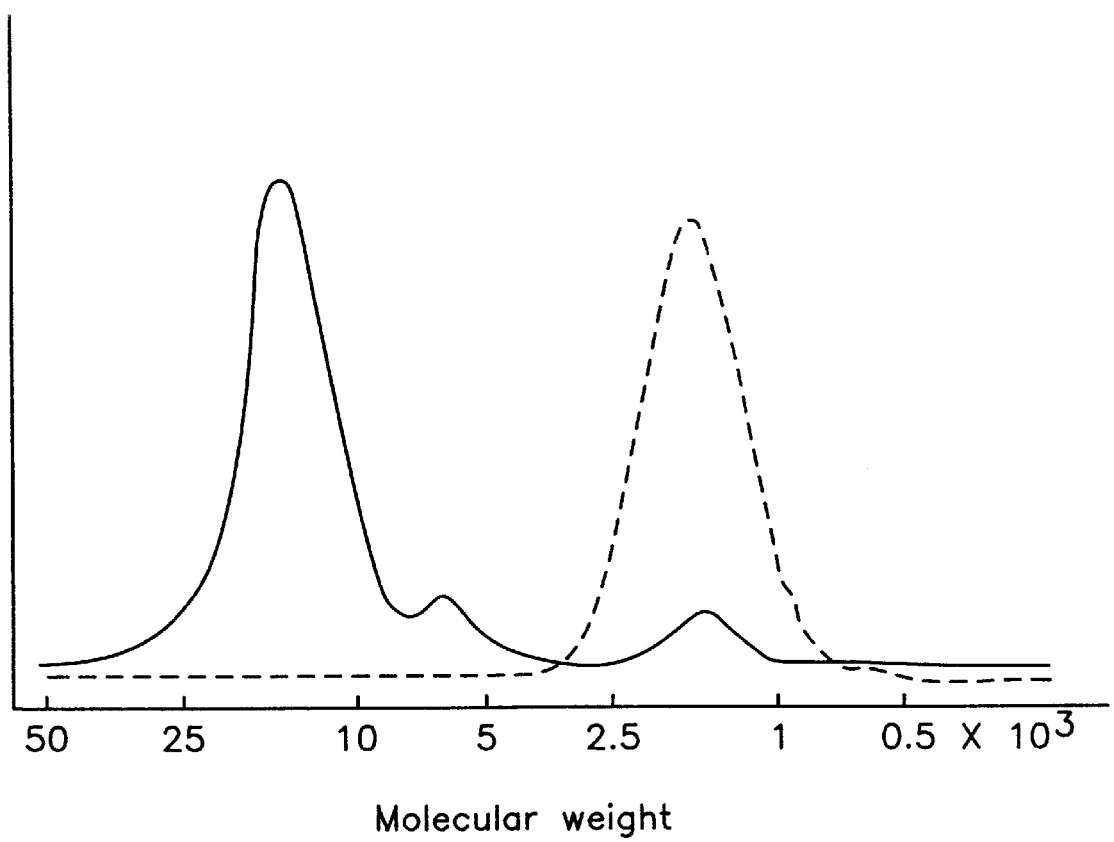
FIG. 10 is the results of gel filtration analysis of the silane copolymer obtained in Example 10 and the raw material used in Example 10.

The results of gel filtration analysis of the resulting silane copolymer and the raw material, silylated hydrolyzed silk protein, are shown in FIG. 10. As apparent from FIG. 10, in the resulting silane copolymer, a peak corresponding to a gel filtration molecular weight of about 1600 of the raw material, silylated hydrolyzed silk protein, nearly disappeared, and a large peak was recognized corresponding to a gel filtration molecular weight of about 15000. Namely, copolymerization of the silylated hydrolyzed silk protein with the silane compound was recognized.

Parts of the resulting copolymer and the raw material, silylated hydrolyzed silk protein, were respectively analyzed by FT-IR and the results were compared. A peak near 1250 cm$^{-1}$ became stronger, and a peak near 1100 cm$^{-1}$ was detected. Namely, it was recognized that the resulting silane copolymer has a Si—O—Si linkage.

EXAMPLE 11

100 g of a 30% aqueous solution of a silylated hydrolyzed silk protein represented by the general formula (VII), wherein, $R^5=CH_3$, $R^6$ and $R^7=OH$, connecting moiety A is —$(CH_2)_3$—, average of q=0.06, average of r=9.94, and average of q+r=10 (number average molecular weight 1250, 0.024 mol), was charged into a 500 ml beaker, and pH thereof was controlled to 3 with dilute hydrochloric acid. A mixture of 6.4 g of dimethyldiethoxysilane (0.048 mol, 2 equivalent per silylated hydrolyzed silk protein) and 1.9 g of 50% ethanol solution of dimethyloctadecyl-[(3 - trimethoxysilyl)-propyl]ammonium chloride (0.002 mol, 0.08 equivalent per silylated hydrolyzed silk protein) was added to the solution with stirring on a hot water bath at 50° C. over 1.5 hours. After completion of the addition, the stirring was continued for 5 hours at 50° C. Then, pH thereof was controlled to 7 with an aqueous sodium hydroxide solution, and the solution was stirred for 6 hours at 50° C. to conduct polycondensation.

To this solution was added dropwise 11 g (0.1 mol) of trimethylchlorosilane over 30 minutes and the mixture was stirred. During this operation, pH of the solution was maintained from 7 to 8 by adding a 20% aqueous sodium hydroxide solution dropwise simultaneously. After completion of the addition, the mixture was further stirred for 3 hours to complete the reaction.

After completion of the reaction, impurities were removed from the reaction solution by filtration, and the concentration was controlled to obtain 115 g of a 30% aqueous solution of a silane copolymer of a silylated hydrolyzed silk protein and a silane compound.

Figure 11:
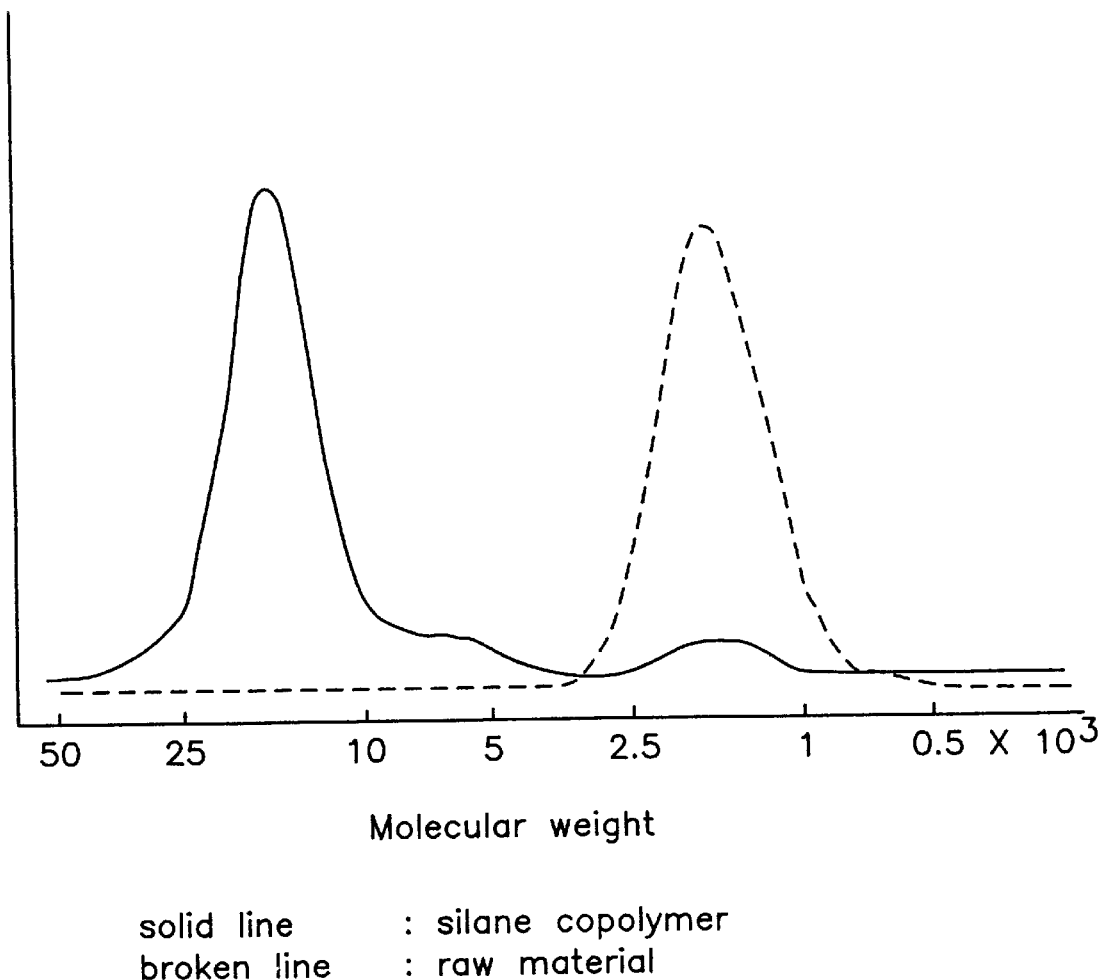
FIG. 11 is the results of gel filtration analysis of the silane copolymer obtained in Example 11 and the raw material used in Example 11.

The results of gel filtration analysis of the resulting silane copolymer and the raw material, silylated hydrolyzed silk protein, are shown in FIG. 11. As apparent from FIG. 11, in the resulting silane copolymer, a peak corresponding to a gel filtration molecular weight of about 1600 of the raw material, silylated hydrolyzed silk protein, nearly disappeared, and a large peak was recognized corresponding to a gel filtration molecular weight of about 16000. Namely, copolymerization of the silylated hydrolyzed silk protein with the silane compound was recognized.

Parts of the resulting copolymer and the raw material, silylated hydrolyzed silk protein, were respectively analyzed by FT-IR and the results were compared. A peak near 1250 cm$^{-1}$, which is believed to be derived from Si—CH$_3$ became stronger, and a peak near 1100 cm$^{-1}$, which is believed to be derived from Si—O was detected. Namely, it was recognized that the resulting silane copolymer has a Si—O—Si linkage.

EXAMPLE 12

Measurement of Smoothness of Hair Surface Treated with Silane Copolymer Obtained in Examples Hair was treated with the silylated peptide-silane copolymer obtained in the above-described examples 1 to 11, and the smoothness of the hair surface was measured according to the following method.

10% aqueous solutions were prepared using the above-described silane copolymer obtained in Examples 1 to 11 and raw material, silylated peptides. 1 g of hair having a length of 10 cm was immersed in the solution for 10 minutes, and the hair was dried by a hair drier. As comparisons, hair was treated with 10% aqueous solutions of the raw material, that is, silylated hydrolyzed collagen, silylated hydrolyzed keratin, silylated hydrolyzed soybean protein, silylated hydrolyzed yeast protein, and silylated hydrolyzed silk used in Examples 1 to 11, and smoothness thereof was tested.

The smoothness of the hair surface was measured using an friction sensitive tester, KES-SE manufactured by Kato Tech Co., Ltd. In this apparatus, the smoothness (roughness) is represented by the average deviation of friction factor which is felt by a friction sensor moving on the surface of a sample in certain distance, the unit is dimensionless, and lower value indicates higher smoothness.

The average deviation of friction factor when a friction sensor moved 2 cm on the surface of each sample is shown in Table 3. The measured value is an average value of 10 measured values for each sample.

TABLE 3

| | Average deviation of friction factor | |
| --- | --- | --- |
| | Resulting silane copolymer | Raw material, silylated peptide |
| Example 1 | 0.2712 | 0.2996 |
| Example 2 | 0.2705 | 0.2996 |
| Example 3 | 0.2814 | 0.3049 |
| Example 4 | 0.2822 | 0.3049 |

TABLE 3-continued

| | Average deviation of friction factor | |
|---|---|---|
| | Resulting silane copolymer | Raw material, silylated peptide |
| Example 5 | 0.2653 | 0.2948 |
| Example 6 | 0.2850 | 0.3056 |
| Example 7 | 0.2845 | 0.3056 |
| Example 8 | 0.2907 | 0.3114 |
| Example 9 | 0.2898 | 0.3114 |
| Example 10 | 0.2636 | 0.2922 |
| Example 11 | 0.2633 | 0.2922 |
| Untreated hair | 0.3243 | |

As is shown in Table 3, the average deviation of friction factor of the hair surface treated by the silane copolymer obtained in Examples 1 to 11 is lower than the average deviation of friction factor of the untreated hair by 10 to 18% in each case, and when compared with the average deviation of friction factor of hair treated with the raw material used in the examples, silylated peptide, it is lower by 7 to 10%, respectively, and it is apparent that smoothness is imparted to the hair surface.

EXAMPLE 13

Test of Adsorbability onto Hair of Copolymerized Composition

Adsorbability onto hair of the above-described silylated peptide-silane copolymer obtained in Examples 1 to 11 was tested according to the column circulation method in "Damage degree evaluation method of hair (I)" described in Journal of SCCJ Vol. 21, No. 2.

Namely, 1.8 g of hair cut into an average length of 2 mm was filled in a liquid chromatography column having a diameter of 7.5 mm and a length of 75 mm, and a sample solution having a controlled concentration of the silylated peptide-silane copolymer obtained in Examples 1 to 11 of 2% was allowed to circulate through this column for a certain time at a flow rate of 2 ml/min.

The concentration of the sample in the sample solution after the circulation was determined by gel filtration analysis of the sample solution, and the amount of sample adsorption per 1 g of hair was calculated based on the change of the sample concentration in the sample solution before and after the circulation. The reduced amount of the sample concentration by permeation into hair was corrected by using a 2% aqueous solution of a polyoxyethylene glycol having an average molecular weight of 1000 as control and allowing this sample solution to circulate under the same conditions as described above, and regarding the reduced amount of the concentration of the polyoxyethylene glycol as due to permeation into hair.

For comparison, adsorbability onto hair was also tested using 2% aqueous solutions of the raw material, silylated peptides, used in the examples. Adsorbability onto hair of the silane copolymer obtained in Examples 1 to 11 when the circulation time was 15 minutes, 30 minutes, 45 minutes, 60 minutes and 90 minutes are shown in Table 4 in index when the adsorption amount of the raw material onto hair was 100 (part lower than decimal point is rounded off).

TABLE 4

| | Adsorbability onto hair (index) Circulation time (minute) | | | | |
|---|---|---|---|---|---|
| | 15 | 30 | 45 | 60 | 90 |
| Silane copolymer obtained in Example 1 | 126 | 120 | 132 | 127 | 121 |
| Silane copolymer obtained in Example 2 | 106 | 118 | 120 | 119 | 118 |
| Silane copolymer obtained in Example 3 | 115 | 121 | 126 | 126 | 122 |
| Silane copolymer obtained in Example 4 | 118 | 121 | 122 | 122 | 124 |
| Silane copolymer obtained in Example 5 | 122 | 131 | 133 | 131 | 124 |
| Silane copolymer obtained in Example 6 | 122 | 120 | 118 | 117 | 120 |
| Silane copolymer obtained in Example 7 | 108 | 116 | 120 | 121 | 120 |
| Silane copolymer obtained in Example 8 | 106 | 107 | 115 | 117 | 116 |
| Silane copolymer obtained in Example 9 | 104 | 105 | 112 | 116 | 119 |
| Silane copolymer obtained in Example 10 | 192 | 193 | 198 | 212 | 208 |
| Silane copolymer obtained in Example 11 | 165 | 177 | 186 | 194 | 196 |

As apparent from the results shown in Table 4, the silylated peptide-silane copolymers obtained in Examples 1 to 11 had an index showing adsorbability onto hair of over 100, and posesses higher adsorbability than that of each raw material, silylated polypeptide. Particularly, the adsorbability onto hair of the silylated hydrolyzed silk-silane copolymer in Examples 10 and 11 was higher than the raw material.

EXAMPLE 14

Moisture Absorption Property Test of Copolymer

The moisture absorption property of the silylated peptide-silane copolymers obtained in Examples 2, 4, 7–9 and 11 was tested.

Dry pulverized wool was place on a petri dish, the pulverized wool was impregnated with a sample so that the amount of the copolymer components became 0.3 g, and dried in a constant temperature drying vessel until the weight became constant. Then the petri dish was placed in a thermostat chamber having a relative humidity of 79.2%, the weight was measured every 24 hours, and the moisture absorption amount (g) per 1 g of wool was obtained.

As comparison, the moisture absorption amount (g) per 1 g of wool was tested also regarding the silylated peptides used as raw materials in the examples in the same manner as described above. The moisture absorption amount per 1 g of wool in each example 1 day (24 hours), 2 days (48 hours), 3 days (72 hours) and 4 days (96 hours) after the storage is shown in Table 5 in index when the adsorption amount regarding each raw material is 100 (part lower than decimal point is rounded off).

TABLE 5

| | Moisture absorption property Storage period (day) | | | |
|---|---|---|---|---|
| | 1 | 2 | 3 | 4 |
| Silane copolymer obtained in Example 2 | 106 | 108 | 109 | 110 |
| Silane copolymer obtained in Example 4 | 107 | 109 | 109 | 109 |

TABLE 5-continued

| | Moisture absorption property Storage period (day) | | | |
|---|---|---|---|---|
| | 1 | 2 | 3 | 4 |
| Silane copolymer obtained in Example 7 | 110 | 114 | 114 | 117 |
| Silane copolymer obtained in Example 8 | 121 | 121 | 118 | 117 |
| Silane copolymer obtained in Example 9 | 121 | 120 | 120 | 122 |
| Silane copolymer obtained in Example 11 | 104 | 103 | 105 | 106 |

As apparent from the results shown in Table 5, the silylated peptide-silane copolymers obtained in Examples 2, 4, 7–9 and 11 had an index of moisture absorption property indicating moisture retention ability of over 100, and revealed increased moisture retention ability as compared with that of each raw material, silylated peptide. Particularly, the moisture retention ability of the silylated hydrolyzed yeast protein-silane copolymer in Example 9 was higher than that of the raw material silylated hydrolyzed yeast protein.

What is claimed is:

1. A silane copolymer which is obtained by polycondensing one or more organic silane compounds (I) having a hydrophilic group represented by the following general formula (I):

  (I)

wherein m represents 2 or 3, $R^1$ represents an alkoxy group, a hydrogen atom or an alkyl group having 1 to 3 carbon atoms, A is a connecting moiety and represents at least one group selected from the group consisting of a methylene group, propylene group, —$(CH_2)_3OCH_2CH(OH)CH_2$—, —$(CH_2)_3S$—, and —$(CH_2)_3NH$— and B represents a peptide group with one or more silane compounds (III) represented by the following general formula (III):

  (III)

wherein n represents an integer from 0 to 2, p represents an integer from 2 to 4, n+p≦4, $R^2$ represents an organic group in which a carbon atom is directly connected to the silicon atom and when n is 2, the two R groups may be the same or different, and Y represent at least one group selected from the group consisting of an alkoxy group, hydrogen atom and siloxy group and when 4-p-n is 2, the Y groups may be the same or different.

2. The silane copolymer according to claim 1 which is obtained by further reacting with one or more silane compounds represented by the following general formula (V):

  (V)

wherein, $R^3$ represent an organic group in which a carbon atom is directly connected to the silicon atom and the three $R^3$ groups may be same or different.

3. The silane copolymer according to claim 1, wherein one or more silane compounds represented by the general formula (III) is obtained by hydrolyzing a silane compound represented by-the following general formula (II):

  (II)

wherein n represents an integer from 0 to 2, $R^2$ represents an organic group in which a carbon atom is directly connected to the silicon atom and when n is 2, the two $R^2$ groups may be the same or different, and X represent at least one group selected from the group consisting of a hydroxyl group, alkoxy group, halogen group, carboxyl group and amino group and the two or more X groups may be the same or different.

4. The silane copolymer according to claim 2, wherein one or more silane compounds represented by the general formula (III) is obtained by hydrolyzing a silane compound represented by the following general formula (II):

  (II)

wherein n represents an integer from 0 to 2, $R^2$ represents an organic group in which a carbon atom is directly connected to the silicon atom and when n is 2, the two $R^2$ groups may be the same or different, and X represent at least one group selected from the group consisting of a hydroxyl group, alkoxy group, halogen group, carboxyl group and amino group and the two or more X groups may be the same or different; and one or more silane compounds represented by the general formula (V) is obtained by hydrolysis of a silane compound represented by the following general formula (IV):

  (IV)

wherein, $R^3$ represent an organic group in which a carbon atom is directly connected to the silicon atom and the three $R^3$ groups may be same or different, and Z represents at least one group selected from the group consisting of a hydroxyl group, alkoxy group, halogen group, carboxyl group and amino group.

5. The silane copolymer according to claim 1, wherein the peptide has a number average molecular weight of 100–50,000.

6. A cosmetic which comprises the silane copolymer according to claim 1.

7. A cosmetic according to claim 6, which is applied to hair or skin.

8. A cosmetic which comprises the silane copolymer according to claim 2.

9. A cosmetic according to claim 8 which is applied to hair or skin.

10. A method for producing a silane copolymer which comprises a step of polycondensing one or more organic silane compounds (I) having a hydrophilic group represented by the following general formula (I):

  (I)

wherein m represents 2 or 3, $R^1$ represents an alkoxy group, a hydrogen atom or an alkyl group having 1 to 3 carbon atoms, A is a connecting moiety and represents at least one group selected from the group consisting of a methylene group, propylene group, —$(CH_2)_3OCH_2CH(OH)CH_2$—, —(CH$_2$)$_3$S—, and —(CH$_2$)$_3$NH— and B represents a peptide group with one or more silane compounds (III) represented by the following general formula (III):

$$R^2{}_n Si(OH)_p Y_{(4-p-n)} \quad \text{(III)}$$

wherein n represents an integer from 0 to 2, p represents an integer from 2 to 4, n+p≦4, R$^2$ represents an organic group in which a carbon atom is directly connected to the silicon atom and when n is 2, the two R groups may be the same or different, and Y represent at least one group selected from the group consisting of an alkoxy group, hydrogen atom and siloxy group and when 4-p-n is 2, the Y groups may be the same or different.

11. The method for producing a silane copolymer according to claim 10 which further comprises a step of reacting one or more silane compounds represented by the following general formula (V):

$$R^3{}_3 Si(OH) \quad \text{(V)}$$

wherein, R$^3$ represent an organic group in which a carbon atom is directly connected to the silicon atom and the three R$^3$ groups may be same or different, with the resulting silane copolymer obtained by polycondensing the organic silane compounds of the formula (I) with the silane compounds of the formula (III).

12. The method for producing a silane copolymer according to claim 10, which further comprises a preliminary step of hydrolyzing a silane compound represented by the following general formula (II):

$$R^2{}_n SiX_{(4-n)} \quad \text{(II)}$$

wherein n represents an integer from 0 to 2, R$^2$ represents an organic group in which a carbon atom is directly connected to the silicon atom and when n is 2, the two R groups may be the same or different, and X represent at least one group selected from the group consisting of a hydroxyl group, alkoxy group, halogen group, carboxyl group and amino group and the two or more X groups may be the same or different to obtain one or more silane compounds represented by the general formula (III).

13. The method for producing a silane copolymer according to claim 11, which further comprises a step of hydrolyzing a silane compound represented by the following general formula (II):

$$R^2{}_n SiX_{(4-n)} \quad \text{(II)}$$

wherein n represents an integer from 0 to 2, R$^2$ represents an organic group in which a carbon atom is directly connected to the silicon atom and when n is 2, the two R$^2$ groups may be the same or different, and X represent at least one group selected from the group consisting of a hydroxyl group, alkoxy group, halogen group, carboxyl group and amino group and the two or more X groups may be the same or different to obtain an organic silane compound represented by the general formula (III) is;

and a step of hydrolyzing a silane compound represented by the following general formula (IV):

$$R^3{}_3 SiZ \quad \text{(IV)}$$

wherein, R$^3$ represent an organic group in which a carbon atom is directly connected to the silicon atom and the three R$^3$ groups may be same or different, and Z represents at least one group selected from the group consisting of a hydroxyl group, alkoxy group, halogen group, carboxyl group and amino group to obtain a silane copound represented by the general formula (V).

14. The method for producing a silane copolymer according to claim 10, wherein B in the general formula (I) represents a peptide having a number average molecular weight of 100–50,000.

15. The method for producing a silane copolymer according to claim 4, wherein B in the general formula (I) represents a peptide having a number average molecular weight of 100–50,000.

* * * * *